United States Patent
Pawliszyn et al.

(10) Patent No.: US 9,733,234 B2
(45) Date of Patent: Aug. 15, 2017

(54) PROBE FOR EXTRACTION OF MOLECULES OF INTEREST FROM A SAMPLE

(71) Applicants: Janusz B. Pawliszyn, Waterloo (CA); German Augusto Gomez Rios, Waterloo (CA)

(72) Inventors: Janusz B. Pawliszyn, Waterloo (CA); German Augusto Gomez Rios, Waterloo (CA)

(73) Assignee: JP SCIENTIFIC LIMITED, Waterloo (CA)

( * ) Notice: Subject to any disclaimer, the term of this patent is extended or adjusted under 35 U.S.C. 154(b) by 14 days.

(21) Appl. No.: 14/738,688

(22) Filed: Jun. 12, 2015

(65) Prior Publication Data

US 2015/0318160 A1 Nov. 5, 2015

Related U.S. Application Data

(60) Continuation-in-part of application No. 14/705,238, filed on May 6, 2015, which is a continuation of
(Continued)

(51) Int. Cl.
*G01N 1/02* (2006.01)
*G01N 30/00* (2006.01)
(Continued)

(52) U.S. Cl.
CPC ............ *G01N 33/50* (2013.01); *B01J 20/286* (2013.01); *G01N 1/405* (2013.01);
(Continued)

(58) Field of Classification Search
CPC ........ G01N 1/405; G01N 1/02; G01N 33/521; G01N 30/00; G01N 30/6078;
(Continued)

(56) References Cited

U.S. PATENT DOCUMENTS 4,140,653 A 2/1979 Imura et al.
4,476,231 A 10/1984 Deindoerfer
(Continued)

FOREIGN PATENT DOCUMENTS

CN 102698720 10/2012
DE 19905239 8/2000
(Continued)

OTHER PUBLICATIONS

Smith et al., "Solid-Phase Microextraction as a Tool For Studying Volatile Compounds in Frog Skin", Chemistry and Ecology, 2000, vol. 17, pp. 215-225.
(Continued)

*Primary Examiner* — David A Vanore
(74) *Attorney, Agent, or Firm* — Borden Ladner Gervais LLP; David A. Nauman

(57) ABSTRACT

A device is described for generating ionized molecules for analysis in a mass spectrometer. The device includes: a solid substrate having one or more edges and a coated area that is coated with an extraction phase comprising an extraction polymer. The solid substrate may have at least two edges that meet at an angle from about 8° to about 180°. Mass spectrometry systems that include such a device are also described. Methods of analyzing a molecule previously extracted from a sample onto the device are also described.

19 Claims, 14 Drawing Sheets

Related U.S. Application Data application No. 13/478,295, filed on May 23, 2013, now abandoned, which is a division of application No. 12/174,494, filed on Jul. 16, 2008, now abandoned, which is a continuation-in-part of application No. 11/706,167, filed on Feb. 15, 2007, now Pat. No. 8,008,064, which is a continuation of application No. 11/208,933, filed on Aug. 23, 2005, now Pat. No. 7,232,689, which is a continuation-in-part of application No. 10/506,827, filed as application No. PCT/CA03/00311 on Mar. 6, 2003, now Pat. No. 7,384,794.

(60) Provisional application No. 61/997,938, filed on Jun. 13, 2014, provisional application No. 60/364,214, filed on Mar. 11, 2002, provisional application No. 60/393,309, filed on Jul. 3, 2002, provisional application No. 60/421,001, filed on Oct. 25, 2002, provisional application No. 60/421,510, filed on Oct. 28, 2002, provisional application No. 60/427,833, filed on Nov. 21, 2002.

(51) Int. Cl.
*H01J 49/16* (2006.01)
*G01N 33/50* (2006.01)
*G01N 1/40* (2006.01)
*H01J 49/04* (2006.01)
*B01J 20/286* (2006.01)
*A61B 10/00* (2006.01)
*G01N 30/06* (2006.01)
*G01N 30/72* (2006.01)

(52) U.S. Cl.
CPC ........ *H01J 49/0409* (2013.01); *H01J 49/168* (2013.01); *A61B 10/0045* (2013.01); *G01N 30/7233* (2013.01); *G01N 2030/009* (2013.01); *G01N 2030/062* (2013.01); *G01N 2560/00* (2013.01); *Y10T 428/2933* (2015.01)

(58) Field of Classification Search
CPC ............ G01N 30/7233; A61B 10/0045; A61B 5/150343; A61B 5/150358; B82Y 30/00; B01L 3/5023; B01L 3/5085
USPC ............ 530/415; 210/656; 422/70, 551; 250/282, 288, 281, 423 R; 427/214, 215, 427/387, 532; 436/527, 541
See application file for complete search history.

(56) References Cited

U.S. PATENT DOCUMENTS

| | | | |
|---|---|---|---|
| 4,616,652 A | 10/1986 | Simpson | |
| 5,047,437 A | 9/1991 | Cooke et al. | |
| 5,120,510 A | 6/1992 | Gourley et al. | |
| 5,424,187 A | 6/1995 | Shor et al. | |
| 5,460,813 A | 10/1995 | Leung | |
| 5,464,395 A | 11/1995 | Faxon et al. | |
| 5,479,923 A | 1/1996 | Rantala | |
| 5,640,470 A | 6/1997 | Iyer et al. | |
| 5,691,206 A | 11/1997 | Pawliszyn | |
| 5,693,228 A | 12/1997 | Koehler et al. | |
| 5,808,300 A * | 9/1998 | Caprioli | H01J 49/0004 250/281 |
| 6,027,942 A | 2/2000 | Hutchens et al. | |
| 6,287,521 B1 | 9/2001 | Quay et al. | |
| 6,360,588 B1 | 3/2002 | Ross | |
| 6,555,813 B1 | 4/2003 | Beecher et al. | |
| 6,558,958 B1 | 5/2003 | Pilevar | |
| 6,689,603 B2 | 2/2004 | Pompidou et al. | |
| 6,730,096 B2 | 5/2004 | Basta | |
| 6,743,180 B1 | 6/2004 | Van Bockel | |
| 6,808,937 B2 | 10/2004 | Ligler | |
| 6,871,556 B2 | 3/2005 | Andresen et al. | |
| 7,019,288 B2 | 3/2006 | Becker | |
| 7,125,580 B2 | 10/2006 | Miller et al. | |
| 7,151,167 B2 * | 12/2006 | Gjerde | B82Y 30/00 210/656 |
| 7,232,689 B2 | 6/2007 | Pawliszyn | |
| 7,259,019 B2 | 8/2007 | Pawliszyn et al. | |
| 7,384,794 B2 | 6/2008 | Pawliszyn | |
| 7,468,281 B2 | 12/2008 | Kallury et al. | |
| 7,537,803 B2 * | 5/2009 | Wang | A61K 9/5089 264/11 |
| 7,605,003 B2 | 10/2009 | Chan | |
| 7,667,010 B2 * | 2/2010 | Gjerde | G01N 1/34 210/656 |
| 8,008,064 B2 | 8/2011 | Pawliszyn et al. | |
| 8,148,161 B2 | 4/2012 | Higgins et al. | |
| 8,206,902 B2 | 6/2012 | Mitani et al. | |
| 8,362,219 B2 * | 1/2013 | Gjerde | G01N 1/34 210/656 |
| 8,399,055 B2 * | 3/2013 | Bakry | B01J 20/3242 204/479 |
| 8,598,325 B2 * | 12/2013 | Pawliszyn | G01N 1/405 436/541 |
| 9,108,217 B2 * | 8/2015 | Hoerr | A61L 27/34 |
| 2002/0034827 A1 | 3/2002 | Singh et al. | |
| 2003/0135195 A1 | 7/2003 | Jimenez et al. | |
| 2003/0180954 A1 | 9/2003 | Riviere et al. | |
| 2003/0183758 A1 | 10/2003 | Colburn et al. | |
| 2004/0005582 A1 | 1/2004 | Shipwash | |
| 2004/0171169 A1 | 9/2004 | Kallury et al. | |
| 2004/0224362 A1 * | 11/2004 | Gjerde | B82Y 30/00 435/7.1 |
| 2004/0241721 A1 * | 12/2004 | Gjerde | G01N 1/34 435/6.12 |
| 2005/0032237 A1 | 2/2005 | Sandra et al. | |
| 2005/0112650 A1 | 5/2005 | Chang et al. | |
| 2005/0133714 A1 | 6/2005 | Vestal et al. | |
| 2005/0142033 A1 | 6/2005 | Glezer et al. | |
| 2005/0276727 A1 * | 12/2005 | Pawliszyn | A61B 5/14514 422/537 |
| 2008/0023630 A1 | 1/2008 | Boschelli et al. | |
| 2009/0026122 A1 | 1/2009 | Pawliszyn et al. | |
| 2014/0017693 A1 * | 1/2014 | Mao | A61B 10/0045 435/6.12 |
| 2015/0231602 A1 | 8/2015 | Pawliszyn | |
| 2015/0318158 A1 | 11/2015 | Pawliszyn et al. | |
| 2015/0318160 A1 * | 11/2015 | Pawliszyn | H01J 49/0409 250/282 |

FOREIGN PATENT DOCUMENTS

| | | |
|---|---|---|
| EP | 1618592 | 1/2006 |
| JP | 1164277 | 5/1999 |
| WO | 9115745 | 10/1991 |
| WO | 0068665 | 11/2000 |
| WO | 2010008450 | 1/2010 |

OTHER PUBLICATIONS

Whang et al., "Solid phase microextraction coupled to capillary electrophoresis", Anal. Commun., 1998, 35, pp. 353-356.

Yang et al., "Surface Modification and Blood Compatibility of Polyacrylonitrile Membrane with Immobilized Chitosan-Heparin Conjugate ", Journal of Polymer Research 9: 2002, pp. 201-206, http://www.springerlink.com/content/m2878p248r41nk81/.

Zhang et al.. "Solid-Phase Microextraction", Analytical Chemistry, vol. 66, No. 17, Sep. 1, 1994, pp. 844-853.

Non-final Office Action dated Apr. 4, 2011 from corresponding U.S. Appl. No. 12/939,360.

English translation of Japanese Office Action dated Feb. 10, 2009 from corresponding Appl. No. 574050/2003.

Shirey, Robert E., "Optimization of Extraction Conditions and Fiber Selection for Semivolatile Analytes Using Solid-Phase Microextraction", Journal of Chromatographic Science, Jul. 2000, vol. 38, pp. 279-288.

(56) References Cited

OTHER PUBLICATIONS

Lambropoulou et al., "Validation of an SPME method, using PDMS, PA, PDMS-DVB, and CW-DVB SPME fiber coatings, for analysis of organophosphorus insecticides in natural waters", Anal Bioanal Chem, 2002. vol. 374, pp. 932-941.
Mullett et al., "Direct Determination of Benzodiazepines in Biological Fluids by Restricted-Access Solid-Phase Microextraction", Anal. Chem., 2002, vol. 74, pp. 1081-1087.
Mindrup, et al: "Improved Performance of SPME Fibers and Applications", SUPELCO 2001, Sigma-Aldrich Co. 2001, pp. 1-25.
Musteata, et al. "Biocompatible solid-phase microextraction coatings based on polyacrylonitrile and solid-phase extraction phases." Anal. Chem. 2007, vol. 79, pp. 6903-6911.
Musteata, Mihaela. "Biocompatible solid phase microextraction." Master Thesis, University of Waterloo, 2006. pp. i-xi and 1-70.
Wang, et al. "Surface confined ionic liquid as a stationary phase for HPLC.," Analyst 2006, vol. 131, pp. 1000-1005.
Non-final Office Action from U.S. Appl. No. 13/478,295 dated Feb. 11, 2015.
Restriction Requirement dated Oct. 9, 2014 from U.S. Appl. No. 13/478,295.
Boos et al. Alkyl-diol silica (ADS): restricted access precolumn packing for direct injection and coupled-column chromatography of biofluids. Fesenius J Anal Chem 1995, vol. 352, pp. 684-690.
Restriction Requirement dated Nov. 17, 2008 from corresponding U.S. Appl. No. 11/706,167.
Non-final Office Action dated Aug. 2, 2010 from corresponding U.S. Appl. No. 11/706,167.
Non-final Office Action dated Jan. 21, 2011 from corresponding U.S. Appl. No. 11/706,167.
Notice of Allowance dated Jun. 16, 2011 from corresponding U.S. Appl. No. 11/706,167.
Restriction Requirement dated Apr. 28, 2011 from corresponding U.S. Appl. No. 12/174,494.
Non-final Office Action dated Aug. 29, 2011 from corresponding U.S. Appl. No. 12/174,494.
Final Office Action dated Jan. 20, 2012 from corresponding U.S. Appl. No. 12/174,494.
Advisory Action dated Mar. 22, 2012 from corresponding U.S. Appl. No. 12/174,494.
Non-final Office Action dated Jun. 25, 2014 from corresponding U.S. Appl. No. 12/174,494.
Non-final Office Action dated Jun. 30, 2005 from corresponding U.S. Appl. No. 10/506,827.
Final Office Action dated Dec. 28, 2005 from corresponding U.S. Appl. No. 10/506,827.
Non-final Office Action dated May 30, 2006 from corresponding U.S. Appl. No. 10/506,827.
Final Office Action dated Oct. 26, 2006 from corresponding U.S. Appl. No. 10/506,827.
Non-final Office Action dated May 29, 2007 from corresponding U.S. Appl. No. 10/506,827.
Final Office Action dated Oct. 18, 2007 from corresponding U.S. Appl. No. 10/506,827.
Notice of Allowance dated Jan. 30, 2008 from corresponding U.S. Appl. No. 10/506,827.
Restriction Requirement dated Oct. 28, 2005 from corresponding U.S. Appl. No. 11/206,804.
Non-final Office Action dated Jan. 9, 2006 from corresponding U.S. Appl. No. 11/206,804.
Final Office Action dated Jul. 12, 2006 from corresponding U.S. Appl. No. 11/206,804.
Non-final Office Action dated Jan. 12, 2007 from corresponding U.S. Appl. No. 11/206,804.
Notice of Allowance dated May 16, 2007 from corresponding U.S. Appl. No. 11/206,804.
Restriction Requirement dated Dec. 1, 2005 from corresponding U.S. Appl. No. 11/208,933.
Non-final Office Action dated Mar. 27, 2006 from corresponding U.S. Appl. No. 11/208,933.
Non-final Office Action dated Aug. 9, 2006 from corresponding U.S. Appl. No. 11/208,933.
Final Office Action dated Jan. 3, 2007 from corresponding U.S. Appl. No. 11/208,933.
Notice of Allowance dated Feb. 20, 2007 from corresponding U.S. Appl. No. 11/208,933.
Non-final Office Action dated Apr. 1, 2011 from corresponding U.S. Appl. No. 12/938,876.
Notice of Allowance dated Jan. 11, 2012 from corresponding U.S. Appl. No. 12/938,876.
Notice of Allowance dated Nov. 10, 2011 from corresponding U.S. Appl. No. 12/939,360.
Restriction Requirement dated Jan. 22, 2013 from corresponding U.S. Appl. No. 13/412,122.
Non-final Office Action dated Apr. 8, 2013 from corresponding U.S. Appl. No. 13/412,122.
Final Office Action dated Jul. 25, 2013 from corresponding U.S. Appl. No. 13/412,122.
Notice of Allowance dated Sep. 13, 2013 from corresponding U.S. Appl. No. 13/412,122.
Communication from European Examining Division dated Oct. 23, 2006 from corresponding European Patent Application No. 03706179.3.
Communication from European Examining Division dated Jan. 24, 2007 from corresponding European Patent Application No. 03706179.3.
Communication from European Examining Division dated Dec. 17, 2007 from corresponding European Patent Application No. 03706179.3.
Communication from European Examining Division dated Apr. 29, 2008 from corresponding European Patent Application No. 03706179.3.
Intention to Grant from European Examining Division dated Aug. 19, 2008 from corresponding European Patent Application No. 03706179.3.
International Search Report and Written Opinion from corresponding PCT Application No. PCT/CA2015/050550 dated Aug. 27, 2015.
International Search Report and Written Opinion from corresponding PCT Application No. PCT/CA2015/050551 dated Aug. 27, 2015.
Deng et al. "Strategies for coupling solid-phase microextraction with mass spectometry", Trends in Analytical Chemistry, 55, pp. 55-67, Mar. 2014.
R. M. Gonzalez-Rodriguez, B. Cancho-Grande, and J. Simal-Gandara, Multiresidue determination of 11 new fungicides in grapes and wines by liquid-liquid extraction/clean-up and programmable temperature vaporization injection with analyte protectants/gas chromatography/ion trap mass spectrometry, Journal of Chromatography A, 2009, vol. 1216, pp. 6033-6042.
K. Banerjee, D.P. Oulka, S. Dasgupta, S.B. Patil, S.H. Patil, R. Savant, and P.G. Adsule, Validation and uncertainty analysis of a multi-residue method for pesticides in grapes using ethyl acetate extraction and liquid chromatography-tandem mass spectrometry, Journal of Chromatography A, 2007, vol. 1173, 1-2, pp. 98-109.
V. Guillet, C. Fave, and M. Montury, Microwave/SPME method to quantify pesticides residues in tomato fruits, Journal of Environmental Science and Health Part B, 2009, vol. 44, pp. 415-422.
J. Oliva, A. Barba, N. Vela, F. Melendreras, and S. Navarro, Multiresidue method for the rapid determination of organophosphorous insecticides in grapes, must and wine, Journal of Chromatography A, 2000, vol. 882, pp. 213-220.
J. Oliva, S. Navarro, A. Barba, and G. Navarro, Determination of chlorpyrifos, penconazole, fenarimol, vinclozolin and metalaxyl in grapes, must and wine by on-line microextraction and gas chromatogaphy, Journal of Chromatography A, 1999, vol. 833, pp. 43-51.
A. J. A. Charlton, and A. Jones, Determination of imisazole and triazole fungicide residues in honeybees using gas chromatography-mass spectrometry, Journal of Chromatography A, 2007, 1141, pp. 117-122.
J. Zeng, J.i Chen, Z. Lin, W. Chen, X. Chen, and X. Wang, Development of polydimethylphenylsiloxane-coated fiber for solid-

(56) References Cited

OTHER PUBLICATIONS phase microextraction and its analytical application of qualitative and semi-quantitative of organochlorine and pyrethroid pesticides in vegetables, Analytica Chimica Acta, 2008, vol. 619, pp. 59-66.

M. Anastassiades, S. J. Lehotay, D. Stajnbaher, and F. J. Schenck, Fast and easy multiresidue method employing acetonitrile extraction/partitioning and "dispersive solid-phase extraction" for the determination of pesticide residues in produce. Journal of AOAC International, 2003, vol. 86, 2, pp. 412-431.

D. Steiniger, G. P.Lu, J. Butler, E. Phillips, and Y. Fintschenko, Determination of Multiresidue Pesticides in Green Tea by Using a Modified QuEChERS Extraction and Ion-Trap Gas Chromatography/Mass Spectrometry, Journal of AOAC International, 2010, vol. 93, 4, pp. 1169-1179.

S. C. Cunha, J. O. Fernandes, A. Alves, and M.B.P.P. Oliveira, Fast low-pressure gas chromatography-mass spectrometry method for the determination of multiple pesticides in grapes, must and wines, Journal of Chromatography A, 2009, vol. 1216, pp. 119-126.

Wong J, C.Y. Hao, K. Zhang, P. Yang, K. Banerjee, D. Hayward, I. Iftakhar, A. Schreiber, K. Tech, C. Sack C, M. Smoker, X.R. Chen, S.C. Utture, and D.P. Oulka, Development and Interlaboratory Validation of a QuEChERS-Based Liquid Chromatography-Tandem Mass Spectrometry Method for Multiresidue Pesticide Analysis, Journal of Agricultural and Food Chemistry, 2010, vol. 58, 10, pp. 5897-5903.

P. Paya, M. Anastassiades, D. Mack, I. Sigalova, B. Tasdelen, J. Oliva, and A. Barba, Analysis of pesticide residues using the Quick Easy Cheap Effective Rugged and Safe (QuEChERS) pesticide multiresidue method in combination with gas and liquid chromatography and tandem mass spectrometric detection. Analytical and Bioanalytical Chemistry, 2007, vol. 389, 6.

Pawliszyn and J. SPME Method Development. Solid Phase Microextraction: Theory and Practice, 1. New York : Wiley-VCH, 1997, pp. 97-139.

S. Risticevic, H. Lord, T. Gorecki, C. L. Arthur, and J. Pawliszyn, Protocol for solid phase microextraction method development, Nature Protocols, 2010, vol. 5, 1, pp. 122-139.

J. Schurek, T. Portoles, J. Hajslova, K. Riddellova, and F. Hernandez, Application of head-space solid-phase microextraction coupled to comprehensive two-dimensional gas chromatography-time-of-flight mass spectrometry for the determination of multiple pesticide residues in tea samples, Analytica Chimica Acta, 2008, vol. 611, 2, pp. 163-172.

D. A. Lambropoulou and T. A. Albanis, Headspace solid-phase microextraction in combination with gas chromatography-mass spectrometry for the rapid screening of organophosphorus insecticide residues in strawberries and cherries, Journal of Chromatography A, 2003, vol. 993, 1-2, pp. 197-203.

M. Natangelo, S. Tavazzi, and E. Benfenati, Evaluation of solid phase microextraction-gas chromatography in the analysis of some pesticides with different mass spectrometric techniques: Application to environmental waters and food samples, Analytical Letters, 2002, vol. 35, 2, pp. 327-338.

W. Chen, KF Poon and M. H. W. Lam, The application of solid phase microextraction in the analysis of organophosphorous pesticides in a food plant, Environmental Science & Technology, 1998, vol. 32, 23, pp. 3816-3820.

K. Fytianos, N. Raikos, G. Theodoridis, Z. Velinova, and H. Tsoukali.,Solid phase microextraction applied to the analysis of organophosphorous insecticides in fruits, Chemosphere, 2006, vol. 65, pp. 2090-2095.

A. Menezes Filho, F, N. Santos, and P. A. P. Pereira, Development, validation and application of a maethodology based on solid-phase micro extraction followed by gas chromatography coupled to mass spectrometry (SPME/GC-MS) for the determination of pesticides residues in mangoes, Talanta, 2010, vol. 81, pp. 346-354.

M. Volante, M. Pontello, L. Valoti, M. Cattaneo, M. Bianchi, and L. Colzani, Application of solid phase microextraction (SPME) to the analysis of pesticides residues in vegetables, Pest Management Science, 2000, vol. 56, pp. 618-636.

H. L. V. Capobiango and Z. L. Cardeal, A solid phase microextraction method for the chromatographic determination of organophosphorous pesticides in fish, water, potatoes, guava and coffee, Journal of Brazilian Chemical Society, 2005, vol. 16, 5, pp. 907-914.

C. G. Zambonin, M. Quinto, N. De Vietro, and F. Palmisano, Solid phase microextraction—gas chromatography mass spectrometry: A fast and simple screening method for the assessment of organophosphorous pesticides residues in wine and fruit juices. Food Chemistry, 2004, vol. 86, pp. 269-274.

C. G. Zambonin, A. Cilenti, F. Palmisano, Solid phase microextraction and gas chromatography-mass spectrometry for the rapid screening of triazole residues in wine and strawberries, Journal of Chromatography A, 2002, vol. 967, pp. 255-260.

A. Aguinaga, N, Campillo, P. Vinas, and M. Hernadez-Cordoba, Solid phase microextraction coupled to gas chromatography-mass spectrometry for the analysis of famoxadone in wines, fruits and vegetables, Spectroscopy Letters, 2009, vol. 42, pp. 320-326.

R. Hu, B. Hennion, L. Urruty, and M. Montury, Solid phase microextraction of pesticide residues from strawberries, Food Additives and Contaminants, 1999, vol. 16, 3, pp. 111-117.

P. Vinas, N. Campillo, N. Martinez-Castillo, and M. Hernandez-Cordoba, Method development and validation for strobilurin fungicides in baby foods by solid phase microextraction gas chromatography-mass spectrometry, Journal of Chromatography A, 2009, vol. 1216, pp. 140-146.

K. Ridgway, S. P. D. Lalljie, and R. M. Smith, Sample preparation techniques for the determination of trace residues and contaminants in food, Journal of Chromatography A, 2007, vol. 1153, pp. 36-53.

F. Augusto, E. Carasek. R. G. C. Silva, S. R. Rivellino, A. D. Batista, and E. Martendal, New sorbents for extraction and microextraction techniques, Journal of Chromatography A, 2010, vol. 1217, pp. 2533-2542.

L. Cai, S. Gong, M. Chen, and C. Wu, Vinyl crown ether as a novel radical crosslinked sol-gel SPME fiber for determination of organousphosphorous pesticides in food samples, Analytica Chimica Acta, 2006, vol. 559, pp. 89-96.

D. Djozan, M. Mahkam, and B. Ebrahimi, Preparation and biding study of solid phase microextraction fiber on the basis of ametryn-imprinted polymer—Application to the selective extraction of persistent triazine herbicides in tap water, rice, maize and onion, Journal of Chromatography A, 2009, vol. 1216, pp. 2211-2219.

E. Turiel, J. L. Tadeo, and A. Martin-Esteban, Molecularly imprinted polymeric fibers for solid phase microextraction. Analytical Chemistry, 2007, vol. 79, pp. 3099-3104.

C. Dietz, J. Sanz, and C. Camara, Recent developments in solid phase microextraction coatings and related techniques, Journal of Chromatography A, 2006, vol. 1103, pp. 183-192.

J. Beltran, F.J. Lopez, and F. Hernandez, Solid-phase microextraction in pesticide residue analysis, Journal of Chromatography A, 2000, vol. 885, pp. 389-404.

A. Jahnke and P. Mayer, Do complex matrices modify the sorptive properties of polydimethylsiloxane (PDMS) for non-polar organic chemicals, Journal of Chromatography A, 2010, vol. 1217, 29, pp. 4765-4770.

D. Vuckovic, R. Shirey, Y. Chen, L. Sidisky, C. Aurand, K. Stenerson, and J. Pawliszyn, In vitro evaluation of new biocompatible coatings for solid-phase microextraction: Implications for drug analysis and in vivo sampling applicatons, Analytica Chimica Acta, 2009, vol. 638, pp. 175-185.

L. S De Jager, G. A. Perfetti, and G. W. Diachenko, Analysis of tetramethylene disulfotetramine in foods using solid-phase microextraction-gas chromatography-mass spectrometry, Journal of Chromatography A, 2008, vol. 1192, pp. 36-40.

A. L. Simplicio and L. V. Boas, Validation of a solid-phase microextraction method for the determination of organophosphorous pesticides in fruits and fruit juice, Journal of Chromatography A, 1999, vol. 833, pp. 35-42.

A. Kloskowski and M. Pilarczyk, Membrane solid-phase microextraction—A new concept in sorbent preparation, Analytical Chemistry, 2009, vol. 81, pp. 7363-7367.

(56) References Cited

OTHER PUBLICATIONS

Frérot et al., "Solid-Phase Microextraction (SPME): A New Tool in Pheromone Identification in Lepidoptera", J. High Resolut. Chromatogr., 1997, vol. 20, pp. 340-342.
Heinze, "Ultramicroelectrodes in Electrochemistry", Angew. Chem. Int. Ed. Engl., 1993, 32, pp. 1268-1288.
Jackson et al., "Mass spectrometry for genotyping: an emerging tool for molecular medicine", Molecular Medicine Today, Jul. 2000, vol. 6, pp. 271-276.
Lavaud et al., "Optimal anticoagulation strategy in haemodialysis with heparin-coated polyacrylonitrile membrane", Nephrology Dialysis Transplantation, 2003, 18, pp. 2097-2104, available at http://ndt.oxfordjournals.org/cgi/content/abstract/18/10/2097V.
Lord et al., "Development and Evaluation of a Solid-Phase Microextraction Probe for in Vivo Pharmacokinetic Studies", Anal. Chem. Oct. 1, 2003, vol. 75, No. 19, pp. 5103-5115.
Moneti et al., "Solid-phase Microextraction of Insect Epicuticular Hydrocarbons for Gas Chromatographic/Mass Spectrometric Analysis", Rapid Communications in Mass Spectrometry, vol. II, 1997 pp. 857-862.
Namera et al., "Analysis of anatoxin-a in aqueous samples of solid-phase microextraction coupled to high-performance liquid chromatography with fluorescence detection and on-fiber derivatization", Journal of Chromatography A, 963, 2002, pp. 295-302.
Nie et al., "Preparation and Characterization of polyacrylonitrile-based membranes: Effects of internal coagulant on poly (acrylonitrile-co-maleic acid) ultrafiltration hollow fiber membranes", Desalination 160 (2004) pp. 43-50.
Alpendurada., "Solid-phase Microextraction: a Promising Technique for Sample Preparation in Environmental Analysis," Journal of Chromatography. A, Aug. 2000, vol. 889(1-2), pp. 3-14.
Chen et al., "Solid Phase Microextraction Coupled to High-Performance Liquid Chromatography," Analytical Chemistry, Aug. 1995, vol. 67 (15), pp. 2530-2533.
Furlong et al., "Routine Determination of Sulfonylurea, Imidazolinone, and Sulfonamide Herbicides at Nanogram-Per-Liter Concentration by Solid-Phase Extraction and Liquid Chromatography/Mass Spectrometry," The Science of the Total Environment, Apr. 2000, vol. 248 (2-3), pp. 135-146.
Hu et al., "Solid-phase Microextraction of Phenol Compounds Using a Fused-silica Fiber Coated With Beta-cyclodextrin-bonded Silica Particles," Analytical Sciences, Apr. 2004, vol. 20 (4), pp. 667-671.
International Patent Application No. PCT/CA2003/000311, International Search Report dated Oct. 10, 2003.
International Patent Application No. PCT/CA2015/050551, International Preliminary Report on Patentability dated Dec. 22, 2016.
Kataoka et al., "Applications of Solid-Phase Microextraction in Food Analysis," Journal of Chromatography A, Jun. 2000, vol. 880 (1-2), pp. 35-62.
Louch et al., "Dynamics of Organic Compound Extraction from Water Using Liquid-Coated Fused Silica Fibers," Analytical Chemistry, May 1992, vol. 64 (10), pp. 1187-1199.
Martos et al., "Calibration of Solid Phase Microextraction for Air Analyses Based on Physical Chemical Properties of the Coating," Analytical Chemistry, Jan. 1997, vol. 69 (2), pp. 206-215.
Poerschmann et al., "Solid Phase Microextraction for Determining the Distribution of Chemicals in Aqueous Matrices," Journal of Analytical Chemistry, Feb. 1997, vol. 69 (4), pp. 597-600.
Reubsaet et al., "Determination of Benzodiazepines in Human Urine and Plasma with Solvent Modified Solid Phase Micro Extraction and Gas Chromatography; Rationalisation of Method Development Using Experimental Design Strategies," Journal of Pharmaceutical and Biomedical Analysis, Dec. 1998, vol. 18 (4-5), pp. 667-680.
Sigma-Aldrich, SPME Sample Prep Made Easy, How to Choose the Proper SPME Fiber, Newsletter, Sigma-Aldrich, Supelco, Supelco Park, Bellefonte, PA 16823-0048, 1999, 4 pages.
U.S. Appl. No. 14/492,411, Office Action dated Feb. 16, 2014.
U.S. Appl. No. 14/705,238, Office Action dated Sep. 7, 2016.
U.S. Appl. No. 14/839,529, Office Action dated Jan. 26, 2017.
U.S. Appl. No. 14/839,529, Restriction Requirement dated Oct. 4, 2016.
Japanese Patent Application No. 574050/2003, Notice of Reasons for Rejection dated Feb. 10, 2009 (English translation).
Mirnaghi et al., "Reusable Solid-Phase Microextraction Coating for Direct Immersion whole-Blood Analysis and Extracted Blood Spot Sampling Coupled with Liquid Chromatography-Tandem Mass Spectrometry and Direct Analysis in Real Time-Tandem Mass Spectrometry", Analytical Chemistry, Aug. 2012, vol. 84 (19), pp. 8301-8309.
U.S. Appl. No. 14/738,678, Non-Final Office Action dated Mar. 22, 2017.
Vail et al., "Rapid and Unambiguous Identification of Melamine in Contaminated Pet Food Based on Mass Spectrometry with Four Degrees of Confirmation", Journal of Analytical Toxicology, Jul./Aug. 2007, vol. 31 (6), pp. 304-312.
Moder et al., Determination of urinary acylcarnitines by ESI-MS coupled with solid-phase microextraction (SPME). Journal of Mass Spectrometry, Jul. 22, 1997, vol. 32, pp. 1195-1204.
U.S. Appl. No. 14/839,529, Final Office Action dated Jun. 12, 2017.

\* cited by examiner

PROBE FOR EXTRACTION OF MOLECULES OF INTEREST FROM A SAMPLE

CROSS REFERENCE TO RELATED APPLICATIONS

This application is a continuation-in-part of U.S. patent application Ser. No. 14/705,238, filed May 6, 2015; which is a continuation of U.S. patent application Ser. No. 13/478, 295, filed May 23, 2012; which is a divisional application of U.S. patent application Ser. No. 12/174,494, filed Jul. 16, 2008; which was a continuation-in-part of U.S. patent application Ser. No. 11/706,167 filed Feb. 15, 2007 (now U.S. Pat. No. 8,008,064); which is a continuation of U.S. patent application Ser. No. 11/208,933 filed Aug. 23, 2005 (now U.S. Pat. No. 7,232,689); which is a continuation-in-part of U.S. patent application Ser. No. 10/506,827 filed Sep. 7, 2004 (now U.S. Pat. No. 7,384,794) which is derived from International Patent Application PCT/CA2003/0000311. Further, this application is entitled to the benefit of, and claims priority to, U.S. Patent Application No. 60/364,214, filed Mar. 11, 2002; U.S. Patent Application No. 60/393,309, filed Jul. 3, 2002; U.S. Patent Application No. 60/421,001, filed Oct. 25, 2002; U.S. Patent Application No. 60/421,510, filed Oct. 28, 2002; and U.S. Patent Application No. 60/427,833 filed Nov. 21, 2002. This application also claims the benefit of priority of U.S. Provisional Patent Application No. 61/997,938 filed Jun. 13, 2014. The entirety of each document is incorporated herein by reference.

FIELD

The present disclosure relates to methods and devices for mass spectrometry analysis of molecules of interest present in a sample.

BACKGROUND

Mass spectrometry is undeniably one of the most important and commonly used analytical tools to detect, identify and quantitate molecules. Given its sensitivity and selectivity, mass spectrometry is particularly important in life science applications. Among the different methods developed up to date for the introduction of the analytes into the mass spectrometer, electrospray ionization (ESI) is acknowledged as the ultimate approach for ionization of molecules in solution phase. Despite its multiple advantages, extensive, expensive and elaborate sample-preparation/separation steps are commonly required to analyze complex sample (e.g. blood, saliva, or urine) by ESI. In order to increase the speed of analysis and minimize the sample treatment, ambient ionization methods were introduced. In essence, the main goal of ambient ionization is to ionize analytes under an ambient environment from condensed-phase samples with minimal or nil sample preparation and/or separation. Thus, these modern techniques offer an attractive solution for real-time and on-site analysis of complex samples. Among this family of techniques, desorption electrospray ionization (DESI) and direct analysis in real time (DART) have become the most established. In essence, these techniques "wipe-off" analytes from the samples by exposing their surfaces to an ionizing medium which is essentially a gas or an aerosol. Although these techniques have provided significant advances in environmental, forensic, clinical and food applications, their operation generally requires sophisticated and costly equipment (e.g. source of high pressure gas for pneumatic assistance, pumping means to provide a continuous flow of a solvent, and feedback-controlled electronics for sample positioning). Other techniques combining sampling and ionization are also being used for these types of analyses, including laser ablation electrospray ionization (LAESI), liquid extraction surface analysis (LESA) and paper spray ionization. Individually these techniques have some advantages, however none of them combine all of these functions in a single apparatus: (i) collecting a sample, (ii) enriching it relative to its initial concentration in the sample, (iii) preparing said sample for analysis, and (iv) ionizing it for analysis by a mass spectrometer. Consequently, an analytical chemistry technique capable of combining sampling, sample preparation, analyte enrichment, and ionization in a single apparatus with simple instrumentation requirements is an unmet need for chemical analysis.

SUMMARY

The present disclosure generally relates to systems and methods to extract or enrich analytes of interest present on a fluid, surface, or tissue, and subsequently generate ions for mass spectrometry. The systems and methods disclosed herein, termed "coated blade spray", include a solid substrate having one or more edges and coated with an extraction phase comprising an extraction polymer, where the solid substrate can be used without further modification as an ionization device for mass spectrometry. The extraction phase may include a solid phase microextraction (SPME) particles. The extraction polymer may be a biocompatible polymer.

The expression "analyte of interest" and "compound of interest" should be understood to be synonymous. In some examples, a compound of interest may be a "chemical of interest" or a "molecule of interest".

In certain aspects, the present disclosure relates to systems and methods for ion generation using a coated solid substrate that substantially prevents the contamination and/or damage of the mass spectrometer analyzer because the systems and methods extracts the analytes of interest while discarding sample components such as proteins, carbohydrates, salts and detergents.

Devices and methods described herein use a solid substrate coated with an extraction polymer. The solid substrate is preferably substantially flat. The solid substrate may have a pointed end. The pointed end of the solid substrate may have an angle from 8° to 90°. The solid substrate may have an end that is curved or elliptical. In preferred examples, the solid substrate has a pointed end that has an angle from 20° to 60°. The solid substrate is preferably coated with sufficient extraction polymer to result in a coated area of at least 0.01 mm$^2$. In various examples, the area is from about 0.1 mm$^2$ to about 100 mm$^2$, and preferably about 25 mm$^2$. Since the amount of analyte is proportional to the amount of coating on the solid substrate, a substrate having a coated area less than 0.1 mm$^2$ will still generate ions, but the signal may not last for a desirable time. The extraction polymer may be a biocompatible polymer.

The solid substrate may have a thickness of a few micrometers to a few millimeters. For example, the solid substrate may have a thickness from about 0.01 mm to 2 mm (that is, about 10 µm to about 2000 µm). The solid substrate preferably has a thickness of about 500 µm or less. The thicker the solid substrate, the greater the chance of irreproducible results between substrates. The thinner the solid substrate, the greater the chance that the solid substrate will be damaged. A solid substrate with a thickness of about 300

μm to about 500 μm provides operational benefits in view of these drawbacks. Solid substrate according to the present disclosure may be square or rectangular in cross-section.

In some preferred examples, the solid substrate has a length from about 1 to about 10 cm; a width from about 0.1 mm to about 5 mm; and a thickness from about 100 micrometers to about 2 millimeters. In particularly preferred examples, the length is about 4 cm, the width is about 2 mm, and/or the thickness is about 500 micrometers. Solid substrates having these preferred dimensions allow the substrates to be used with high-throughput instruments.

Although the present disclosure may use the term "blade" when discussing the solid substrate, a skilled person would understand that features associated with cutting edges (such as blades for knives, swords, or saws) or other devices that includes blades (such as ice skates or oars) are not implied to be a part of the solid substrate of the present disclosure.

As an SPME device, the devices and methods simultaneously isolate and enrich the analytes present in a fluid. Coatings used in the present disclosure may stabilize analytes that are extracted therein. Since the coating can be adjusted towards analytes of interest, devices and methods disclosed herein may reduce undesirable artefacts that might provide ion suppression or enhancement. Since the sample is not placed in front of the mass spectrometer, devices and methods disclosed herein provide sample normalization.

The coated solid substrate may be used as a substrate in various ionization methods, such as in DART (Direct Analysis in Real Time), DESI (Desorption Electrospray Ionization), SELDI (Surface Enhanced Laser Desorption Ionization), MALDI (Matrix-Assisted Laser Desorption Ionization), Liquid Extraction Surface Analysis (LESA), Liquid Microjunction Surface Sampling Probe (LMJ-SSP), or LAESI (laser ablation electrospray ionization). DART and DESI are atmospheric pressure ion source that ionizes gases, liquids and solids in open air under ambient conditions. SELDI and MALDI are soft ionization techniques that use a laser to obtain ions of the analytes. In electrospray-based devices, ions of the extracted or pre-concentrated analytes are generated directly from the edges of the solid substrate by wetting the coated solid substrate with a solvent and applying a high electric field to the wetted substrate.

Another aspect of the present disclosure provides a system for analyzing a sample where the system includes a probe including a coated solid substrate connected to a high voltage source, in which the coated solid substrate is kept discrete from a flow of solvent, and a mass analyzer. It would be understood by a skilled person that a coated solid substrate kept discrete from a flow of solvent means that the coated solid substrate is not connected on a continuous basis to a flow of solvent during the ionization and mass analysis processes. Rather, a specific amount of solvent is applied to the coated solid substrate prior to ionization of the analyte. This solvent is referred to as the "desorption solvent", in contrast to any solvent or solution used for washing or rinsing the coated solid substrate. In other aspects, the present disclosure provides a system for analyzing a sample where the system includes a probe including a coated solid substrate connected to a high voltage source, in which the solid substrate is disconnected in all cases from a flow of solvent. The mass analyzer can be packaged as part of a laboratory bench-top mass spectrometer, or a field-deployable mass spectrometer. Representative mass analyzers include a rectilinear ion trap, a cylindrical ion trap, a quadrupole ion trap, a time-of-flight, an ion cyclotron resonance trap, and an electrostatic ion trap (for example an Orbitrap mass analyzer).

The substrate may include a metal, a metal alloy, or a polymer substrate, such as an electrically conductive polymer substrate. The substrate may include, for example, stainless steel, nitinol, nickel, titanium, aluminum, brass, iron, bronze, or polybutylene terephthalate. It is particularly beneficial to use a metal with shape memory properties (such as nitinol) when the coated solid substrate is used in a method that includes insertion into a tissue or agitation at high speeds. Using a metal with shape memory properties in such methods enables the substrate to maintain, for example, a flat shape. In other examples, the polymer substrate may include a material synthesized from one or more reagents selected from the group consisting of styrene, propylene, carbonate, ethylene, acrylonitrile, butadiene, vinyl chloride, vinyl fluoride, ethylene terephthalate, terephthalate, dimethyl terephthalate, bis-beta-terephthalate, naphthalene dicarboxylic acid, 4-hydroxybenzoic acid, 6-hyderoxynaphthalene-2-carboxylic acid, mono ethylene glycol (1,2 ethanediol), cyclohexylene-dimethanol, 1,4-butanediol, 1,3-butanediol, polyester, cyclohexane dimethanol, terephthalic acid, isophthalic acid, methylamine, ethylamine, ethanolamine, dimethylamine, hexamthylaminediamine (hexane-1,6-diamine), pentamethylenediamine, methylethanolamine, trimethylamine, aziridine, piperidine, N-methyl-piperideine, anhydrous formaldehyde, phenol, bisphenol A, cyclohexanone, trioxane, dioxolane, ethylene oxide, adipoyl chloride, adipic, adipic acid (hexanedioic acid), sebacic acid, glycolic acid, lactide, caprolactone, aminocaproic acid and blends of two or more materials synthesized from the polymerization of these reagents.

Devices and methods of the present disclosure may combine sampling, sample preparation and analyte isolation or enrichment with the ionization process needed for mass spectrometry analysis of samples (such as solids, gels or liquids). Device and methods of the present disclosure may allow for quick analysis of chemicals in samples without compromising sample clean-up needed for mass spectrometry analysis. The sample may be a complex matrix, such as a biofluid, a surface, or a tissue. In particular examples, devices and methods of the present disclosure allow for the quick analysis of water-based salt solution, plasma or urine. In other examples, devices and methods of the present disclosure allow for analysis of analytes in human or animal tissue, such as in vivo tissue. The flat, coated solid substrate may be inserted into the tissue where the coated substrate extracts the analytes present in the tissue. As discussed above, ions of the extracted analytes may be generated directly from the edges of the substrate by applying a high electric field to a pre-wetted coated solid substrate.

Devices and methods of the present disclosure may be used to isolate and enrich analytes of interest by immersing the coated solid substrate into the fluid or tissue of interest, or by spotting the fluid or tissue of interest onto the coated solid substrate. For example, a droplet or droplets comprising a biological fluid (for example blood or lysed cells) may be placed on the coated solid substrate. Analytes of interest are transported from the sample to the coated solid substrate by the interaction between the coated solid substrate and the fluid. The interaction between the coated solid substrate and the fluid or tissue can be from a few seconds to several hours. The rate of extraction or enrichment of analytes of interest from the sample may be increased by agitating the sample at high speed (e.g. vortex agitation). The extraction or enrichment may be performed from samples enclosed in a container, where the volume of the container may be, for example, from a few microliters to a few liters. Alternatively, the extraction or enrichment may be performed from environmental samples (such as lake or sewer water) that are not enclosed in a container. The coated solid substrate may be rinsed one or more times to remove artefacts (e.g. fibers, proteins, cells, particulate matter, detergents, salts) potentially adhered to the coating surface without desorbing the analytes previously extracted or enriched. The coated solid substrate may be rinsed using a solvent that does not desorb the analyte from the coating. In particular examples, the solvent may be water, such as LC/MS grade water. The coated solid substrate may be rinsed a sufficient number of times to substantially eliminate components of the sample (such as salts, lipids, or proteins) that may interfere with the ionization or mass analysis processes. If a solvent is used that does not desorb the analyte, the coated substrate can be rinsed multiple times with substantially no loss of the extracted analyte from the coating.

A discrete amount of a desorption solution, e.g., a droplet or droplets, may be applied to the coated solid substrate when the analyte is to be desorbed in the mass analyzer using high voltage. In examples where the analyte is ionized using other methods, such as MALDI, a desorption solution is not applied. The desorption solution, for example a solvent or a mixture of solvents, is capable of diffusing into the coating. The desorption solution may be applied as a droplet or droplets, and in an amount sufficient to wet the coated solid substrate. The desorption solution may be added in sufficient quantity to form a thin liquid film over the surface of the coating. Once applied to the coated solid substrate, the desorption solution extracts at least a portion of the analytes previously adsorbed by the coating layer. The desorption and ionization of analytes depends on at least the following: the chemistry of the analyte and its affinity for the desorption solution; the partition between the coating layer and the desorption solution (elution efficiency of the analytes), and spray efficiency of the desorption solution at the tip of the substrate. Probes according to the present disclosure may further include an additional housing surrounding the coated portion of the probe to enhance the desorption of the analyte by preventing evaporation of the desorption solvent and/or facilitating generation of electrospray from the tip of the coated solid substrate.

In order to account for variations during mass analysis (such as during electrospray ionization), an internal standard may be included in the coating layer, or the desorption solution may contain an internal standard. The internal standard may, for example, be spiked directly into the sample prior to the extraction or enrichment process in order to account for differences during the extraction among samples and between devices. The internal standard may be preloaded on the coating prior to the extraction of the analytes of interest. Alternatively, internal standards may be included in both the coating prior to the extraction of the analytes and in the sample prior to the extraction.

A holder may be provided for the accurate positioning of the coated solid substrate in front of the orifice or ion-transfer capillary in order to efficiently transmit ionized molecules into the mass spectrometer. The holder has a spring loading based-system, which allows straightforward connection of the high voltage (HV) to the solid coated substrate and its easy and fast replacement between experiments. The holder is constructed using a low-conductive chemically inert material, for example materials used in 3D printing. Specific examples of contemplated materials include, e.g. Teflon, poly(methyl methacrylate), acrylonitrile butadiene styrene (ABS), polycarbonate-ISO (PC-ISO), polycarbonate (PC), polycarbonate-acrylonitrile butadiene styrene (PC-ABS), polyetherimide (such as ULTEM™), and polyphenylsulfone (PPSF). The spring loading system may include a spring loaded screw that can be manufactured with a highly conductive metal or a metal alloy, e.g. stainless steel. In particular examples, the holder is installed on a customized 3D-translation stage that not only adjusts the position with high precision on each dimension, but also accurately tunes the angle at which the solid coated substrate is placed in front of the mass spectrometer. Depending on the ionization method being used, different parts of the solid coated substrate can be placed in front of the instrument to obtain characterization of the analyte distribution on the surface of the substrate. This "scanning" of the probe may be used to study inhomogeneity of analyte distribution in the sample, such as a tissue sample, which produces an "imprint" during extraction process. Ionization methods that allow different parts of the solid coated substrate to be ionized separately include DESI, DART, LESA, LMJ-SSP, and LAESI.

Devices and methods of the present disclosure can be used to perform extraction or enrichment of analytes of interest from different fluids, surfaces, or tissues independently of the sample characteristics (e.g. volume, structure, complexity, and viscosity). The mechanical strength provided by various examples of the coated solid substrate, such as by coated solid substrates thicker than 300 µm, reduces deformation or damage of the solid substrate independently of the sample dimensions, viscosity, or the agitation conditions use for the extraction or enrichment, e.g. speed of agitation. Analogous to other solid phase microextraction geometries, the coated solid substrate can be inserted, introduced into tissue for in vivo monitoring of endogenous and exogenous substances.

Preferred coatings described herein attach to preferred solid substrates with sufficient strength that a corresponding probe may be reused for multiple extraction or enrichment and desorption or ionization cycles with minimal or negligible damage to the coating material or the solid substrate. Such preferred coatings include polyacrylonitrile (PAN). Such preferred solid substrates include stainless steel and nitinol.

A probe according to the present disclosure may be coated with a solid coating that generates ions when solvent and high voltage is applied. In some examples, the coating includes polymeric particles, or a polymeric layer of diverse materials physically or chemically attached to the substrate, for example: octadecyl silane particle or phenyl groups chemically bonded to porous silica particles. A probe may be coated with an extraction phase that covers an area from about 0.1 mm$^2$ to about 100 mm$^2$, and preferably about 25 mm$^2$. Coating thickness should be as thin as possible. When the coating includes particles, the coating should be thick enough to include at least one layer of particles. In preferred examples, the coating includes one or two layers of particles. In particularly preferred examples, the coating includes only a single layer of particles. In some examples, the coating is from about 0.5 to about 100 µm. In some examples, the coating is from 1.7 to 20 µm. Thinner coatings, and coatings with fewer numbers of layers of particles, result in more efficient mass transfer of the analytes (faster extraction and enrichment), but also more effective at desorption or ionization. Octadecyl silane particles with particle size of 5 µm may be used. A substrate according to the present disclosure may be coated with different extraction phases on the two sides of the substrate. The two extraction phases may have different affinities for analytes in the matrix. For example, one side of the substrate may include a coating having extractive particles that provide hydrophobic interactions, while the other side of the substrate may include a coating having extractive particles that provide hydrophilic interactions. Such a coated substrate could be used to extract compounds with two different ranges of polarities.

The coated solid substrate may be reused after a cleaning step. Where the coating corresponds to octadecyl silane particles, the cleaning step may include agitation of the coated solid substrate in a mixture of isopropanol, acetonitrile and methanol. Cleaning step may be changed according to the chemistry of the coating and its affinity towards the analyte of interest. In cases in which there is a vast variability in sample concentration among samples (e.g. low ppt to high ppb or even ppm levels), a coated solid substrate may be used only once to reduce false positives. The sorbing particles can be arranged to form an inhomogeneous distribution along the length of the probe varying either in the particle composition or thickness. For example, the sorbing particles can be a mixture of different particles (such as C18 and HLB particles) and the percent composition of the different particles can vary along the length of the probe.

Both sides of the solid substrate may be coated with the coating. In certain examples, the solid substrate is coated with the same extraction phase on each side and is used to perform reproducible and independent desorption and ionization from each side of the substrate. Duplicate, independent, analysis of the same sample from a single extraction is feasible when the coated solid substrate has the same extraction phase on both sides. In other examples, the solid substrate is coated with a different polymeric phase on each side. The polarity or affinity of the different polymeric phases towards different analytes in the sample can be different. In such a situation, using a solid substrate coated with different extraction phases may provide a more comprehensive analysis in a single extraction.

In certain examples, multiple coated solid substrates can be placed into a holder that provides high-voltage to the coated solids substrates, and enables rapid parallel sampling or sample-preparation. The holder may include a spring loading based-system or a system that includes ball end clamping screws to engage the coated solid substrates. Such systems allow easy and quick replacement of the coated solid substrates. Arranging eight of these holders, where each holder holds 12 coated solid substrates, allows for a concurrent and automated analysis of up to 96 samples in a single run in multi-well-plate format.

As noted above, the holder may include a spring loading based-system or a ball end clamping screw which may be connected to a high voltage source. The system may allow simple connection of the high voltage (HV) to the solid coated substrate and its easy and quick replacement. In certain examples, the holder allows installing multiple independent coated solid substrates simultaneously. In the same example, the holder preferably isolates each coated solid substrate and prevents electrical conductivity among them. In the same example, the holder may allow the connection of high voltage to each coated solid substrate independently. The holder can be fitted on an automated electrical actuator to accurately place each solid substrate in front of the orifice or ion-transfer capillary in order to efficiently transmit ionized molecules to the mass spectrometer. The desorption solvent may be applied as a droplet or droplets, and in an amount sufficient to wet the coated solid substrate, using an automated syringe pump. Both the actuator and the syringe pump may be controlled by the same software/hardware and may be operated concomitantly. The software/hardware that controls the actuator and the syringe pump may also send signal to the mass analyzer in order to start signal acquisition. Hence, a holder fitted on an automated electrical actuator in combination with an automated syringe pump allows performing autonomous desorptions and ionizations from each solid substrate. The system can also be designed to sequentially desorb various portions of each of the probes to obtain information about the distribution of the analytes on the surface of the probe.

BRIEF DESCRIPTION OF THE DRAWINGS

FIG. 1A shows the top view of various exemplary coated solid substrates with a pointed end of different angles. FIG. 1B shows the top view of the coated solid substrates. Coated areas are shown in black, units are given in millimeters.

FIG. 10A is a graph illustrating quantitative analysis of urine spiked with cocaine (500 pg mL$^{-1}$ to 100 ng mL$^{-1}$) and its isotopologue [D3] cocaine (14.5 ng mL$^{-1}$) while FIG. 11A is a graph illustrating quantitative analysis of plasma spiked with cocaine (500 pg mL$^{-1}$ to 100 ng mL$^{-1}$) and its isotopologue [D3] cocaine (14.5 ng mL$^{-1}$) while

DETAILED DESCRIPTION

Figure 1A:
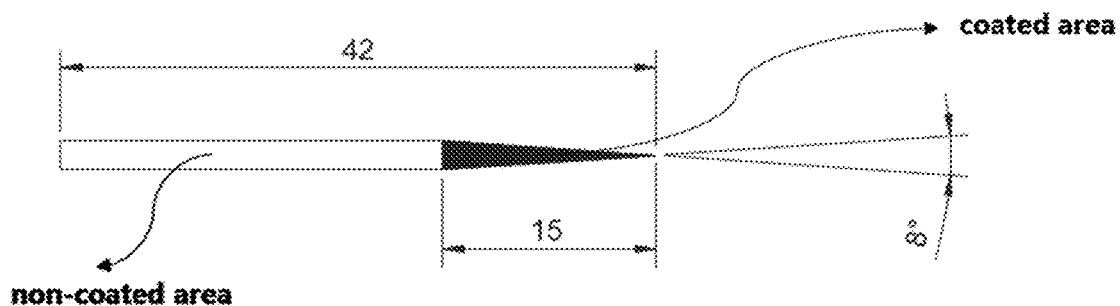
FIGS. 1A-1B are illustrations that depict schematics of possible geometrical configurations of contemplated coated solid substrates.
Figure 1A:
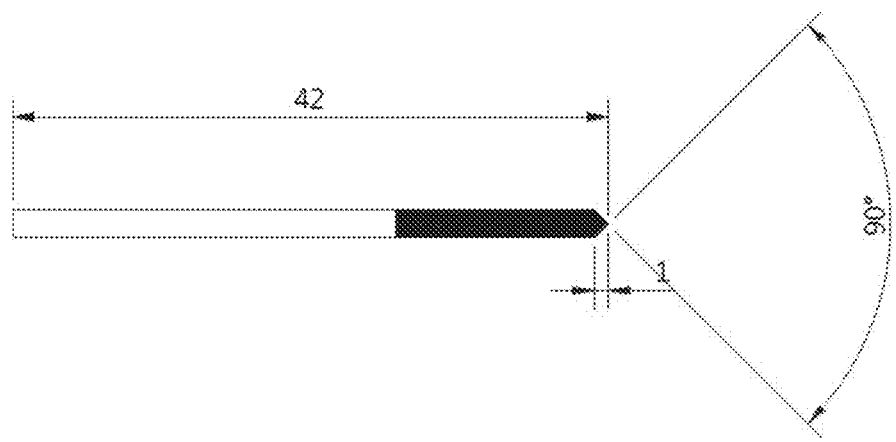

The transitional term "comprising" is synonymous with "including," or "containing," and is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

Ambient ionization methods may be used to increase the speed of analysis and to reduce the sample treatment. Ambient ionization methods ionize analytes under an ambient environment from condensed-phase samples with minimal or no sample preparation and/or separation. Although ambient ionization techniques have represented a revolution in environmental, forensic, clinical and food applications, its operation generally requires sophisticated and costly equipment (e.g. pneumatic assistance, continuous flow of a solvent or a gas, and electronics to control sample positioning). The rapid development of ambient ionization techniques during the beginning of the twenty-first century brought with them a major opportunity for the introduction of new solid phase microextraction (SPME) applications. To date, different geometries of SPME have being coupled to direct analysis in real-time (DART), desorption electrospray ionization (DESI), surface enhanced laser desorption ionization (SELDI), and matrix-assisted laser desorption ionization (MALDI) in a broad range of applications.

There is an unmet need in the scientific community for a green-chemistry technique capable of combining sampling, sample preparation, analyte enrichment and ionization on a single device that does not require intricate instrumentation, such the instrumentation required for pneumatic assistance, continuous flow of a solvent or a gas, or control of sample positioning. The present disclosure relates to systems and methods to extract or enrich analytes of interest present in a fluid or tissue, and subsequently generate ions for mass spectrometry. The present disclosure describes a solid phase micro-extraction (SPME) device that can be used without further modification as an electrospray device for mass spectrometry. The device includes a coated solid substrate and allows for both sample preparation and coupling to mass spectrometry using a single device. The device may include a solid substrate (such as a metal, a metal alloy, or a polymer substrate, e.g. stainless steel, nitinol, or polybutylene terephthalate). The solid substrate is coated with an extraction polymer. When using the coated solid substrate for sample preparation, the coating isolates and enriches the analytes present in the sample. In addition, since the coating preferably adsorbs analytes of interest over other compounds in the sample, clean-up of undesirable artefacts (such as artefacts resulting from fibers, proteins, cells, particulate matter, detergents, and salts) that might provide ion suppression or enhancement is achieved. The coating may include solid phase microextraction particles to adsorb the molecules of interest.

A coated solid substrate according to the present disclosure may be used, for example, as a solid-substrate electrospray ionization source. Ions of the extracted or pre-concentrated analytes are generated by applying a high electric field to coated solid substrate pre-wetted with a small volume (for example a volume≤20 µL) of a desorption solution. In one exemplary method of extracting a compound of interest from a sample and detecting the extracted compound, a coated solid substrate is placed in a methanol:water solution (50:50) at least 15 minutes before extraction in order to improve the interaction between the coating surface and the analytes present in the sample. It should be understood, however, that this conditioning step is not required for all coatings. This conditioning step is, however, preferred when the coating comprises C-18 particles since the conditioning step improves performance of the coating.

The conditioned coated solid substrate is subsequently inserted in a vessel containing the sample and extraction or enrichment of the analyte is performed by agitating the sample at high speed (e.g. vortex agitation at 3200 rpm, t≤1 min). The coated solid substrate is subsequently rapidly rinsed in a vessel containing LC/MS grade water (t≤10 s) to remove at least some of the potential artefacts adhered to the coating surface. It should be understood that multiple rinses in separate rinsing solutions could be used, and that the rinsing time of any of the rinsing solutions could be more or less than 10 seconds. The rinsing time could be, for example, 15, 20 or 30 seconds. However, the total amount of rinsing should be chosen so that there is no significant loss to the amount of analytes adsorbed on the coating.

After the coated solid substrate is rinsed, the coated solid substrate is installed on the holder. The holder, as discussed above, includes a spring loading based-system that connects the coated solid substrate to the high voltage (HV). Other means of applying the HV to the coated solid substrate may alternatively be used. For example, the coated solid substrate may have an electrical lead attached to it to permit the application of the HV during the ionization process. A desorption solution is applied to the coated solid substrate as a droplet or droplets, and in an amount sufficient to wet the coated solid substrate. The droplet or droplets may be delivered by an inject sprayer. A high electric field is applied to the wetted substrate in order to generate ions of the extracted or pre-concentrated analytes directly from the edges of the substrate. The strength of the electric field may be selected based on the ionization configuration. For example, when performing ionization using electrospray ionization at atmospheric pressure, an electric field of a few kV may be applied. In particular examples that use electrospray ionization at atmospheric pressure, an electric field of about 3.5 kV to about 4.5 kV is applied at a distance of about 5 mm from the substrate to the instrument entrance. This corresponds to an electric field of about 700 kV/m to about 900 kV/m. The ionization may take place in negative mode.

In one specific example, analysis of diazepam was performed by applying 17.5 µL of methanol as a desorption solution, allowing the substrate to be wetted for 37.5 s, and applying an electric field of 4 kV to the substrate. However, it is worth emphasizing that these values are valid only for the analysis of diazepam, and other operating parameters may be used in methods to detect other analytes.

In another exemplary method, a coated solid substrate according to the present disclosure is spotted with a biological fluid (for example: blood or lysed cells) or tissue, and subsequently subjected to a freeze-thaw cycle (for example freezing at −80° C. and then thawing). The coated solid substrate is then exposed to a temperature of at least 37° C., thereby disrupting at least some protein-ligand interactions and releasing at least some analytes that were previously bound to proteins, such as albumin or red-blood cells proteins. At least some of the released analytes are extracted by the coating on the solid substrate. The solid substrate is then rinsed, once or more than once as discussed above, and the adsorbed analytes are detected as discussed above, for example by desorbing the analytes using a desorption solution and applying an electric field to the substrate to generate ions for use in electrospray ionization. This exemplary method may allow analytes that are highly bound to proteins, or are present in a complex biological system (such as in lysed cells), to be detected at a lower limit of detection than alternative methods. In the context of the present disclosure, analytes that are highly bound to proteins would be understood to refer to proteins that have bindings above 70%.

Coatings according to the present disclosure can be used for direct microextraction of molecules from a biological matrix, such as fluids or tissues. The biological fluids can be, for example, whole blood, plasma, serum, cerebrospinal fluid, peritoneal fluid, saliva or urine. The tissue could be, for example, isolated cells or organs. The molecules can be hydrophobic or hydrophilic and should preferably weigh less than about 10,000 atomic mass units. The molecules can be drugs or biomarkers. A biomarker is a physiological substance that, when present in abnormal amounts, may indicate the presence of disease.

Coatings used in devices according to the present disclosure can be prepared by covering a solid substrate with a suspension of various extractive particles (for example: C-18/silica, RP-amide/silica, or HS-F5/silica) in a solution of a biocompatible polymer, such as a solution of polyacrylonitrile (PAN), polyethylene glycol, polypyrrole, derivatised cellulose, polysulfone, or polyamide. C-18/silica particles would be understood by one of skill in the art to comprise silica particles derivatized with a hydrophobic phase, the hydrophobic bonded phase comprising octadecyl. For RP-amide-silica particles, the bonded phase comprises palmitamido-propyl. For HS-F5-silica particles, the bonded phase comprises pentafluorophenyl-propyl. The particles can be about 0.2 to about 100 µm particles. Preferably, the particles can be about 0.2 to about 60 µm particles. Preferably, the particles can be about 0.2 to about 30 µm particles. More preferably, the particles can be about 0.2 to about 5 µm particles. The particles can be spherical. The pore size diameter can be about 10 to about 200 Å. Preferably, the pore size can be about 100 to about 180 Å. The surface area can be about 200 $m^2/g$ to about 800 $m^2/g$. Preferably, the surface area can be about 200 $m^2/g$ to about 300 $m^2/g$.

It would be understood by a person of skill in the art that appropriate coatings can be formed with other extractive particles, and particularly with any extractive particles currently used in solid phase extraction or affinity chromatography (e.g. liquid chromatography), depending on the nature of the compound being extracted, in a similar manner than affinity chromatography relies on different particles for separating various compounds. For example, other particles could include such particles as: normal-phase silica, C1/silica, C4/silica, C6/silica, C8/silica, C30/silica, phenyl/silica, cyano/silica, diol/silica, ionic liquid/silica, molecular imprinted polymer particles, hydrophilic-lipophilic-balanced (HLB) particles, carboxen 1006 or divinylbenzene. Mixtures of particles can also be used in the coatings. The particles can be inorganic (e.g. silica), organic (e.g. carboxen or divinylbenzene) or inorganic/organic hybrid (e.g. silica and organic polymer). Furthermore, a person of skill in the art would understand that other biocompatible polymers could be used as glue or support. PAN can also be used for covering existing commercial extraction phases (for example: carbowax/templated resin) with a biocompatible layer.

Coated solid substrates can be used for in vitro analysis of drug concentrations as well as for in vivo analysis of tissue concentrations in a living animal. Coated solid substrates for in vivo analysis can have any combination of extractive particles coated with an appropriate biocompatible coating, such as polyacrylonitrile (PAN), polyethylene glycol, polypyrrole, derivatised cellulose, polysulfone, or polyamide coating. Non-limiting examples of the coating include: a PAN/C-18 coating, a PAN/HLB coating, a PAN/RP-amide coating, a polyethylene glycol/HS-F5 coating, a derivatised cellulose/C-18 coating, a polypyrrole/C-30 coating, a polysulfone/phenyl coating, and a polyamide/cyano coating.

Coated solid substrates according to the present disclosure may be produced through a batch-coating process. In the exemplary batch-coating process, the biocompatible coating is preferably PAN or Polyethylene glycol (PEG). In the exemplary process, a flask type sprayer was used to spray a suspension of extraction particles, suspended in a solution that includes a biocompatible coating, on a surface of the solid substrates. The extraction particles can be C-18, RP-amide, HS-F5 silica particles or any other particle listed above. Mixtures of particles can be used. When the particles are silica particles and the biocompatible coating is PAN, the ratio of PAN/silica can be between 0.3 and 1 wt/wt. The preferred ratio of PAN/silica is 0.65 wt/wt. The ratio is based on the bare weight of silica and adjusted to the phase loading on the silica particles. The biocompatible coating may be dissolved in a solvent. The PAN/solvent solution can be between 5% and 15% PAN (w/w). Preferably, the PAN/solvent solution is between about 5% and about 10% PAN (w/w). More preferably, the PAN/solvent solution is about 7% PAN/solvent (w/w). The solvent can be any solvent known to one of skill in the art that dissolves PAN, for example: dimethylformamide (DMF), dimethyl sulfoxide, NaSCN, $Ca(CNS)_2$, nitric acid, ethylene carbonate or mixtures thereof. More preferably, the solvent can be DMF. The solids substrates may be coated with one layer, or more than one layers, of coating. After applying a layer of coating, the coated substrate can be passed through a heater at an elevated temperature to remove at least a portion of the solvent. The elevated temperature can be from about 120° C.

to about 210° C. Preferably, the elevated temperature is from about 120° C. to about 180° C. A person of skill in the art would readily understand that PAN is fully polymerized when it is dissolved in the solvent and as long as the solvent is fully evaporated, or at least substantially fully evaporated, the blade is properly coated. As such, any means known to a person of skill in the art to remove the solvent can be used to dry the coated substrates.

Multiple thin layers of a coating can be applied to the substrate. For example, a suspension of particles in a biocompatible polymer can be applied to the substrate until the desired coating thickness is obtained. The advantage of applying multiple thin layers, in contrast to applying a single thick layer, is that each coating layer is bonded and the coating thickness is uniform throughout the desired length on the substrate. The process parameters are preferably controlled by automation in order to improve reproducibility between substrates.

Regardless of how coated solid substrates are prepared, uncoated solid substrates can be pre-processed before the coating process in order to clean and roughen the surface. Such pre-processing may further increase the bonding strength between the substrate and the SPME coating. Pre-processing of metal- or metal alloy-based substrates can be accomplished by washing with acetone or methanol, etching for about 30 min to about 60 min in concentrated hydrochloric acid (18-37% vol/vol), washing the substrate with water, thoroughly cleaning the substrate by sonication in water, or any combination thereof (5-120 min). Preprocessing of conductive polymer-based substrates can be accomplished by scraping the material before the coating process in order to clean and roughen the surface.

Prior to use, the coated solid substrates can be conditioned in water:methanol 50:50 wash for 30 min, preferably under agitating conditions (such as at 1200 rpm vortex agitation). Conditioning the C-18 based coatings with water or higher proportion of methanol can lead to reduced reproducibility. Other coatings, however, can require only a very brief conditioning step (less than 5 min), or even none at all.

As discussed above, a desorption solution may be applied to the coated solid substrate to assist in the desorption and the ionization process. Any solvents compatible with mass spectrometry analysis can be used. In particular examples, favorable desorption solutions will be those that are also used for electrospray ionization. Exemplary desorption solutions include combinations of water, methanol, isopropanol, and acetonitrile. They may also include a volatile salt. The organic content (proportion of methanol, acetonitrile, etc. to water), the pH, and volatile salt (e.g. ammonium acetate) may be varied depending on the sample to be analyzed. The composition of a desorption solution may be selected based on the analyte to be desorbed. In particular examples, the desorption solution may be methanol with 0.1% formic acid. In other examples, the desorption solution may include water, acetonitrile, isopropanol, or a combination thereof.

Figure 1B:
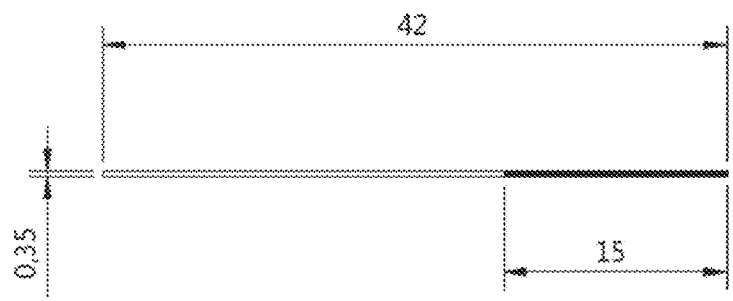

Particular methods according to the present disclosure may generate, using the high electric field, micron scale droplets at an edge of the solid coated substrate. Electrospray ionization at atmospheric (or near atmospheric pressure) benefits from coated solid substrates with sharp features, such as corners, edges, or points. In particular examples, the coated solid substrate is shaped to have a macroscopically sharp point, such as a point of a triangle (e.g. sharp tip of a "gladius sword"), for ion generation. Probes of the invention may have different tip widths. Exemplary coated solid substrates are illustrated in FIGS. 1A and 1B. The illustrated exemplary coated solid substrates are 42 mm long, the coating covers about 15 mm of the length of the substrate, the point of the substrate can be from 8 to 90°, and the substrate is 0.35 mm thick. As mentioned above, no pneumatic assistance is required to transport the droplets. Ambient ionization of analytes is realized on the basis of these charged droplets, offering a simple and convenient approach for mass analysis of analytes previously enriched or pre-concentrated in the solid coated substrate.

Experiment 1

Figure 2:
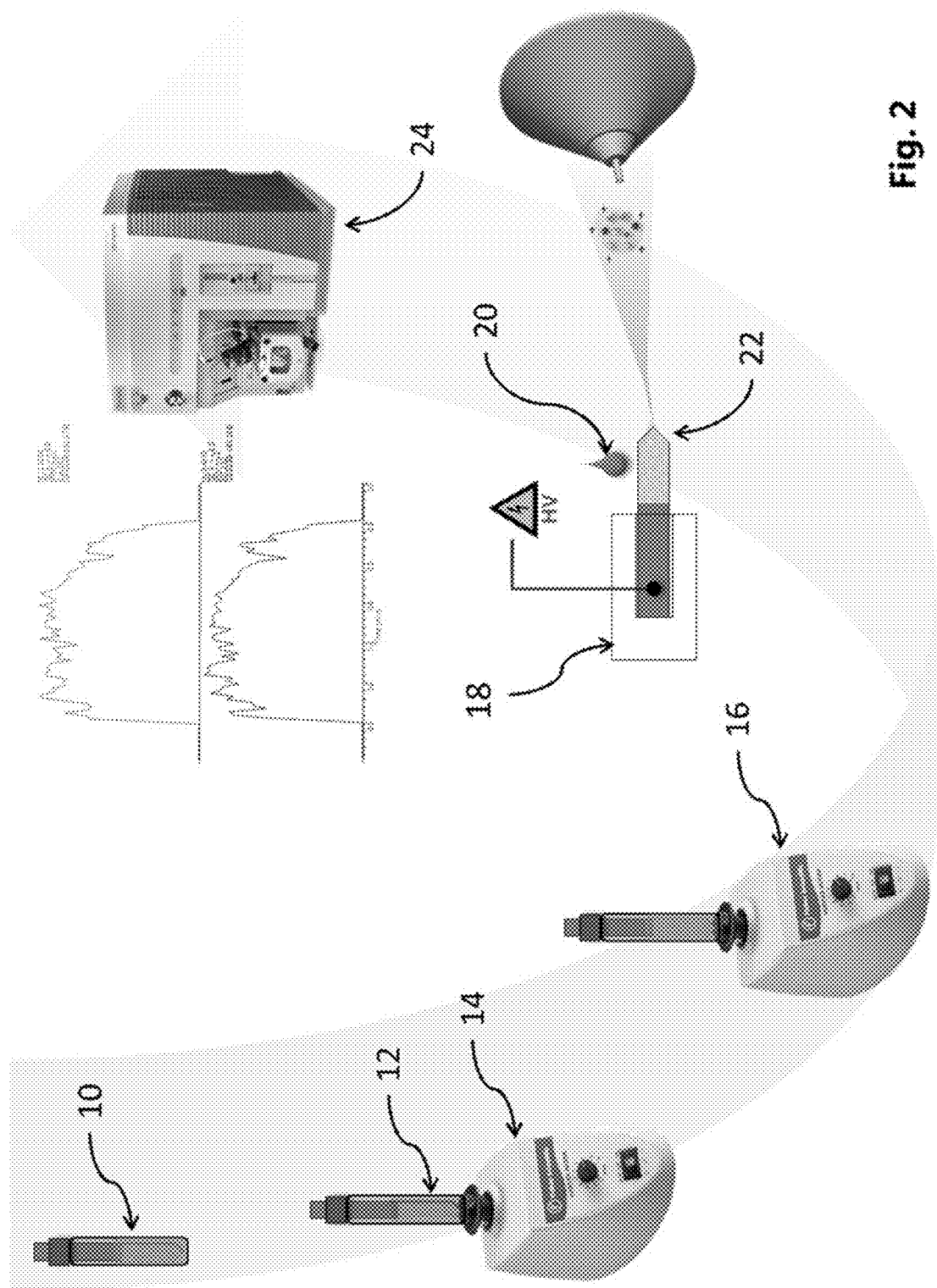
FIG. 2 is an illustration that shows the experimental set up for blade-spray extraction and desorption/ionization.

The analytical process (FIG. 2) includes three steps: a pre-conditioned solid substrate (10) was inserted in a vial (12) containing the sample (300-1500 µL) and quick extraction and enrichment was performed (14) by agitating the sample at high speed (vortex agitation at 3200 rpm, t≤1 min). The coated solid substrate was then rapidly rinsed (16) in a vial containing water (1500 µL, t≤10 s, 3200 rpm vortex agitation) to remove at least some of the artefacts adhered to the coating surface. The coated solid substrate was then installed on a holder (18), in which a ball end clamping screw allowed for straightforward connection of the high voltage (HV) to the blades and their easy and fast replacement between experiments. Then, 17.5 µL of a desorption solution (20) (for example a solvent or a mixture of solvents) was applied to the substrate for about 34 seconds to wet the solid coated substrate and extract and/or concentrate the analytes previously adsorbed by the coating layer. Micron scale droplets were generated at an edge of the solid coated substrate for 30 seconds by applying a 4 kV electrical field to the coated solid substrate (22). The droplets were analyzed (24) by MS/MS using TSQ Vantage/Thermo Oribitrap.

Figure 3A:
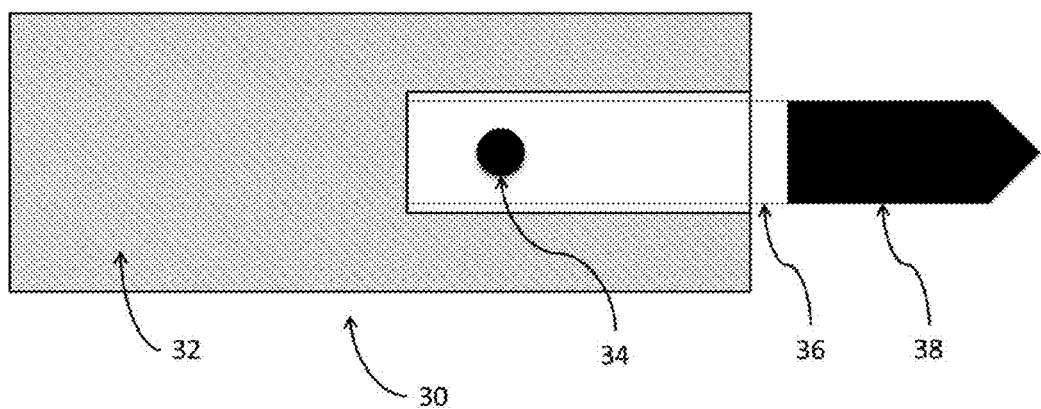
FIGS. 3A and 3B are illustrations that show the top view and lateral views of a schematic of the ball end clamping screws for easy replacement and accurate positioning of a coated solid substrate according to the present disclosure.
Figure 3B:
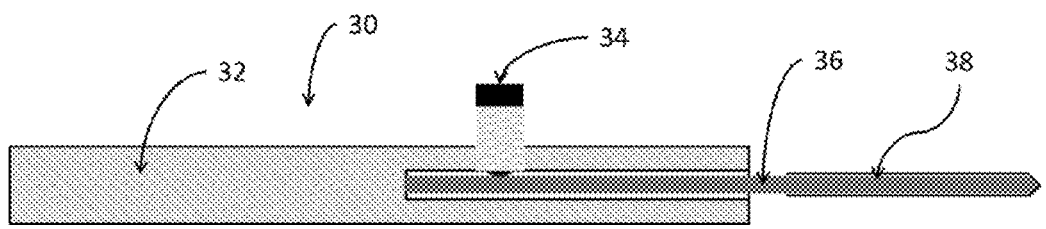

The holder is illustrated in greater detail in FIG. 3A (top view) and FIG. 3B (lateral view). The holder (30) includes a non-conductive holder portion (32) and a ball end clamping screw (34) to hold the coated solid substrate (36). The coated solid substrate includes a coated portion (38).

Figure 4:
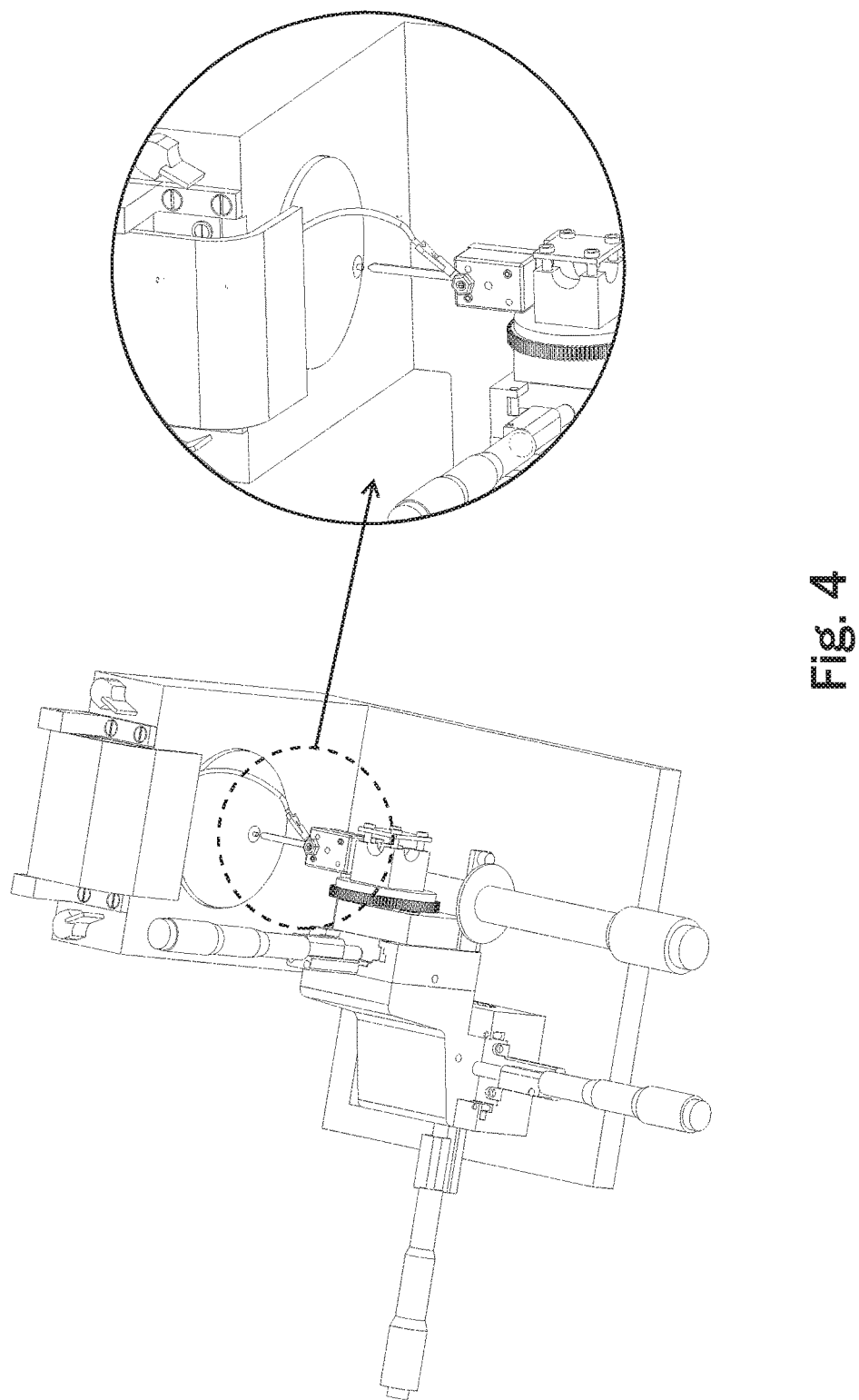
FIG. 4 shows photos of an in-house ionization source for blade spray technology. The 3D-moving stage not only adjusts the position with a precision of 0.02 mm in each dimension (25 mm moving path), but also tunes the spraying tip at different angles on the Z dimension (±0.01° per moving mark). In order to provide reproducible ions transmission, the position of the blade-tip should not be offset more than 2 mm in all the directions from the centre of the ion-transfer capillary.

The holder was installed on a customized 3D-translation stage (photo shown in FIG. 4) that not only adjusts the position with high precision on each dimension, but also accurately tunes the angle at which the solid coated substrate is placed in front of the mass spectrometer.

Experiment 2

Figure 5:
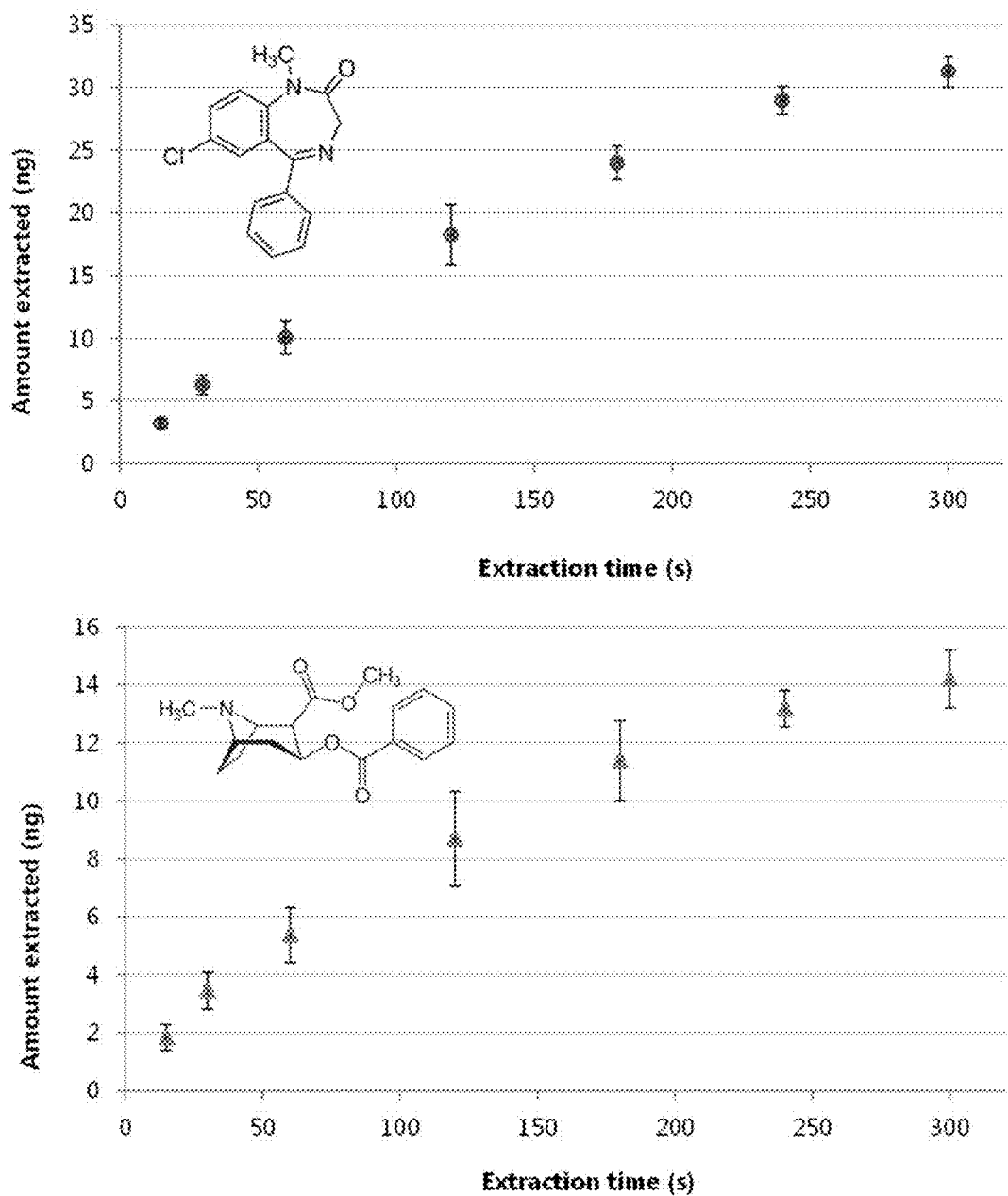
FIG. 5 shows extraction time profile graphs for diazepam and cocaine. Extractions were performed using vortex agitator set-up at maximum speed (3200 rpm). Extractions from 1.5 mL of PBS spiked with 50 ppb of each analyte with 3 different blades (n=6) for each extraction point. Extracts were analyzed using Thermo LC/MS on SRM mode.
Figure 6:
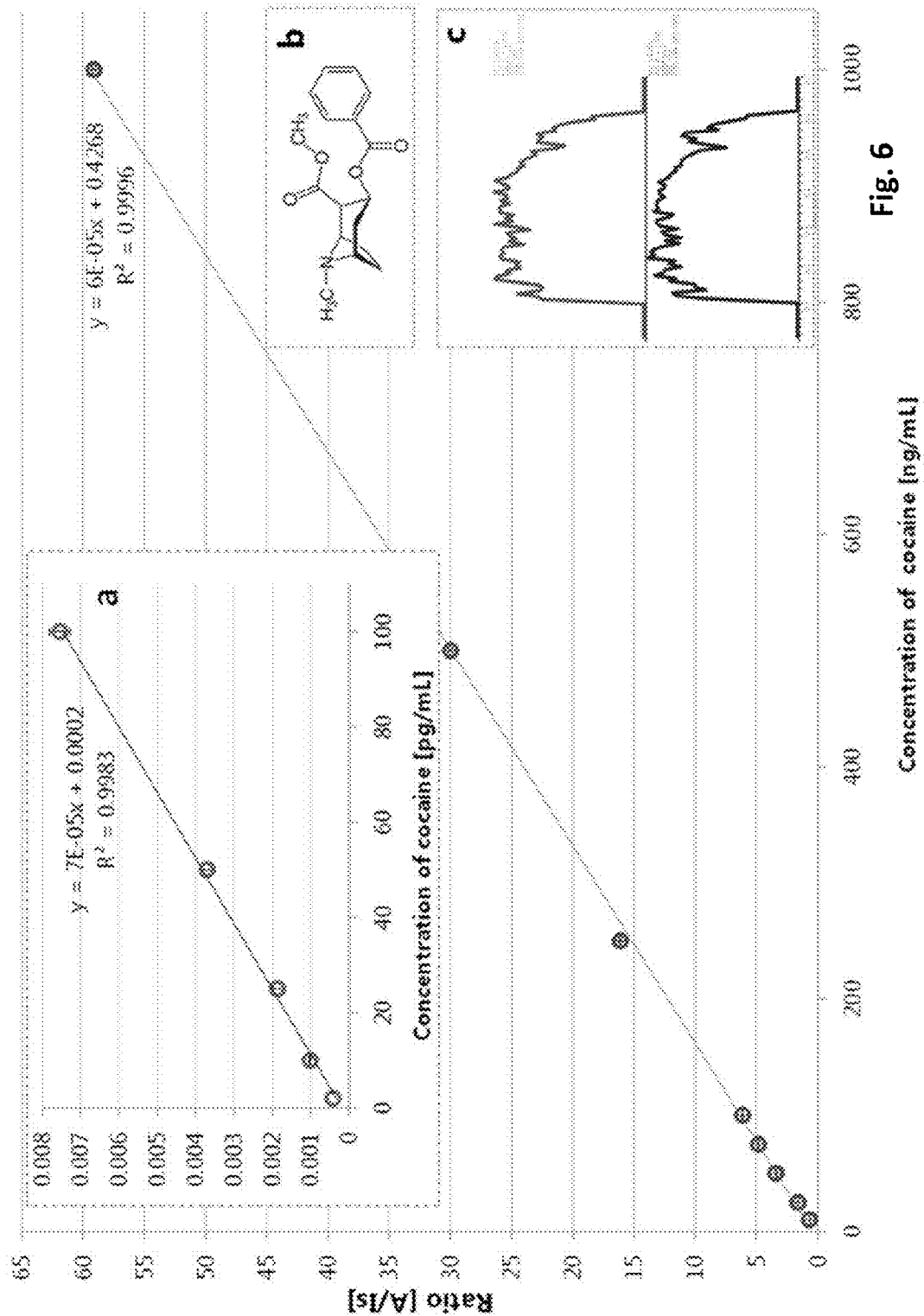
FIG. 6 are graphs illustrating quantitative analysis of PBS spiked with cocaine (2 µg mL$^{-1}$ to 1 µg mL$^{-1}$) and its isotopologue [D3] cocaine (14.5 ng mL$^{-1}$). Bars represent the standard deviation of analysis for three replicates with independent blades. a. Insert plot show low-concentration range; b. Molecular structure of cocaine; c. Ion chronogram of cocaine and [D3] cocaine for 30 seconds acquisition.

Conversely to what is normally believed, SPME extraction or enrichment can be performed in a short period of time and the limits of detection (LOD) of the method is generally constrained by the instrumental capabilities rather than by the intrinsic features of the coating. For instance, as illustrated in FIG. 5, an extraction time of 15 seconds is sufficient to extract a quantifiable amount of diazepam and cocaine. Extraction for longer periods of time, such as up to 300 seconds, allowed for extraction and detection of additional analyte. As can be seen in FIG. 6, a limit of quantification (LOQ) as low as 1 ppt was reached by performing 1 minute extraction using solid substrates coated with C-18/PAN from 1.5 mL of phosphate buffered saline (PBS) spiked with cocaine. Desorption of the analytes was performed using 17.5 µL of acidic methanol (0.1% formic acid). The desorption time was 34 seconds and subsequently a potential of 4 kV was applied to the solid substrate for ionization. The ionized droplets were detected using LC/MS-ESI in positive mode. Furthermore, the linear dynamic range of the exemplary method, evaluated up to 1 ppm, showed astounding linearity. Beyond any doubt, high concentration levels are not a limitation for SPME. Indeed, in cases where affinity of the coating for the analytes is high and analytes are present at concentrations higher than 50 ppb, shorter extraction times (≤30 s) can be performed.

Certainly, direct coupling of SPME to MS using methods according to the present disclosure can surpass detection limits inherent in most SPME-liquid chromatography methods since the desorption and dilution steps associated with liquid chromatography are avoided. In addition, since extractions are carried-out under pre-equilibrium conditions, the amount of analyte collected is controlled by the convection conditions (i.e. boundary layer), the extraction time, and the surface area of the extracting phase. Hence, under an identical sampling setting, blade spray (BS) can exceed sensitivity levels achieved by other SPME geometries owing to its high surface area. By increasing the interaction time between the coating and the sample from 15 seconds to 1 minute, lower LOD can also be achieved.

Experiment 3

Coated solid substrates according to the present disclosure have desirable reusability and intra/inter-device reproducibility characteristics. Extractions performed with three independent blades (n=12) from 1.5 mL of a PBS solution containing 10 ppb of diazepam (DZP) showed intra/inter-blade relative standard deviations (RSD) lower than 1.8% (Table 1). In addition, carry-over was reduced by implementing a cleaning step once the extraction/desorption-ionization cycle was completed. A mixture of methanol (MeOH, 50%), isopropanol (IPA, 25%), and acetonitrile (ACN, 25%) was used to remove most of the residual analytes from preceding extractions. It is worth emphasizing that the cleaning step could be changed according to the chemistry of the coating and the coating's affinity towards the analyte of interest. In cases in which there is a vast variability in sample concentration in different samples (e.g. low ppt to high ppb or even ppm levels), coated substrates could be limited to a single use in order to reduce the possibility that a small amount of analyte (few fg to pg) could remain on the coated substrate after a desorption/cleaning cycle. When working with compounds with high affinity towards the coating and, that are present in the sample at concentrations higher than 50 ppb, it is desirable to use shorter extraction times (for example extraction times of ≤30 s) to diminish the amount of analyte adsorbed by the coating, and to increase the likelihood that substantially no compound remains after the cleaning step. It is also desirable to use thin coatings since thin coatings not only have more efficient mass transfer of the analytes (resulting in shorter extraction times), but also more effective desorption and ionizations.

TABLE 1

Inter- and intra-blade reproducibility (n = 12). Results are reported as ratio of analyte (diazepam) versus internal standard isotopologue [D5] diazepam. 1 min extractions were performed using vortex agitator set-up at maximum speed (3200 rpm). Extraction from 1.5 mL of PBS spiked with 10 ng/mL of each substance. Analyses were performed using Thermo TSQ on SRM mode. Blade spray conditions: 17.5 µL methanol, 3.5 kV, and 37 s wetting time. SD, standard deviation. RSD, relative standard deviation.

| Experiment | Blade-1 | Blade-2 | Blade-3 | Summary |
|---|---|---|---|---|
| 1 | 1.0 | 1.0 | 1.0 | |
| 2 | 1.0 | 1.0 | 1.0 | |

TABLE 1-continued

Inter- and intra-blade reproducibility (n = 12). Results are reported as ratio of analyte (diazepam) versus internal standard isotopologue [D5] diazepam. 1 min extractions were performed using vortex agitator set-up at maximum speed (3200 rpm). Extraction from 1.5 mL of PBS spiked with 10 ng/mL of each substance. Analyses were performed using Thermo TSQ on SRM mode. Blade spray conditions: 17.5 µL methanol, 3.5 kV, and 37 s wetting time. SD, standard deviation. RSD, relative standard deviation.

| Experiment | Blade-1 | Blade-2 | Blade-3 | Summary |
|---|---|---|---|---|
| 3 | 1.0 | 1.0 | 1.0 | |
| 4 | 1.0 | 1.0 | 1.0 | |
| Average | 1.0 | 1.0 | 1.0 | 1.0 |
| SD | 0.02 | 0.02 | 0.01 | 0.01 |
| RSD | 1.8 | 1.7 | 0.7 | 1.3 |

Experiment 4

Figure 7:
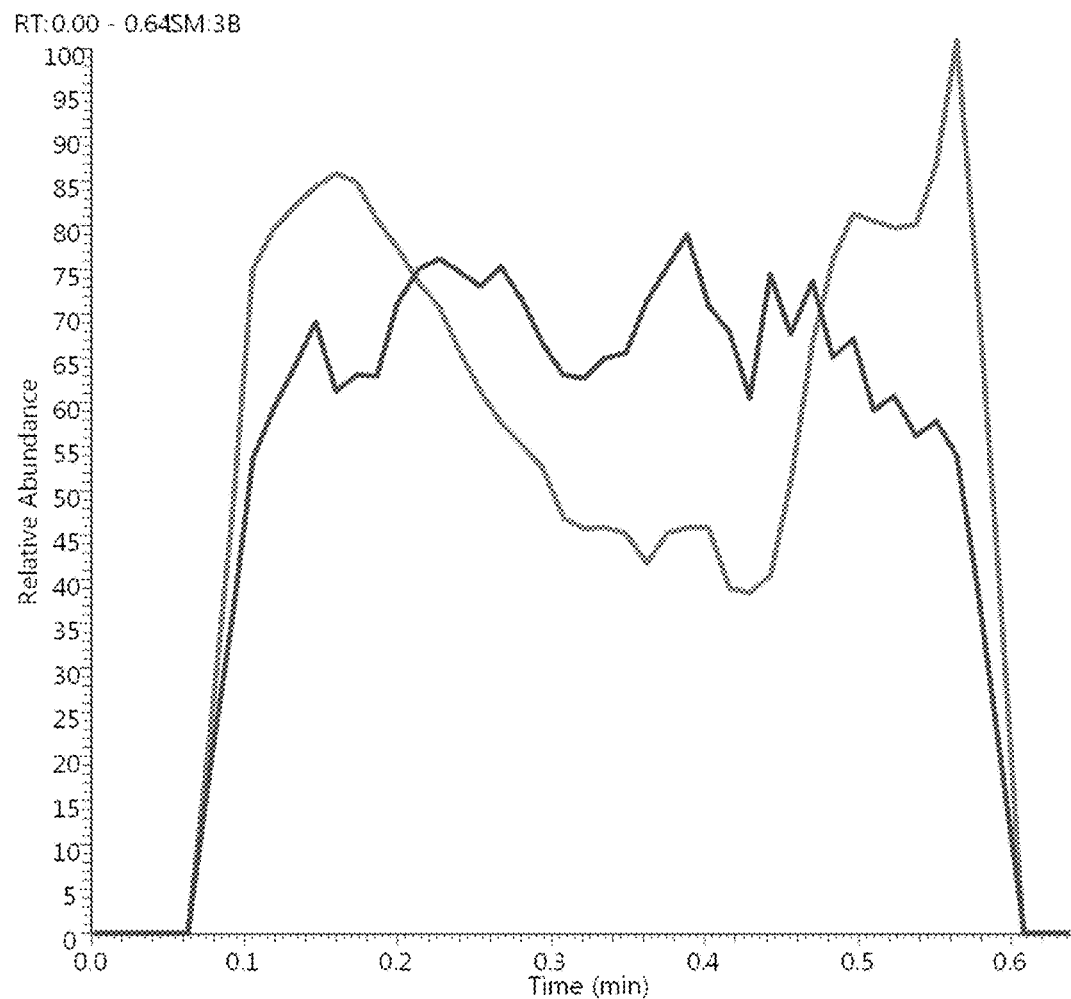
FIG. 7 shows ion chronograms of the cocaine obtained from the desorption/ionization of both sides of the blade (blade spray conditions: 15 µL methanol, 4 kV, and 45 s wetting time). 1 min extractions were performed using vortex agitator set-up at maximum speed (3200 rpm). Extractions from 1.5 mL of PBS spiked with 100 ng mL$^{-1}$ of cocaine using a single blade. Analyses were performed using Thermo Exactive/Orbitrap on full scan mode.

Coated solid substrates according to the present disclosure may be used to perform reproducible and independent desorption/ionization from each side of the blade. Extractions were performed using coated solid substrates coated with C-18/PAN from a vial containing 1.5 mL of plasma spiked with diazepam at 100 ppb. The extraction time was 1 minute at an agitation speed of 3200 rpm (vortex agitation). The desorption of the analytes on the first side of the coated solid substrate was performed using 17.5 µL of acidic methanol (0.1% formic acid). The wetting time was 34 seconds and subsequently a potential of 4 kV was applied to the solid substrate for ionization. Once the first desorption was attained, the blade was flipped over and the desorption solvent was applied to the second side of the coated solid substrate. After 34 seconds, a potential of 4 kV was applied to the solid substrate for ionization and a second ion-chronogram was obtained. The two-ion chronograms are shown in FIG. 7. Hence, analysis in duplicate of each sample from a single extraction is feasible when the substrate is coated with the same extraction phase on both sides.

Experiment 5

Figure 8:
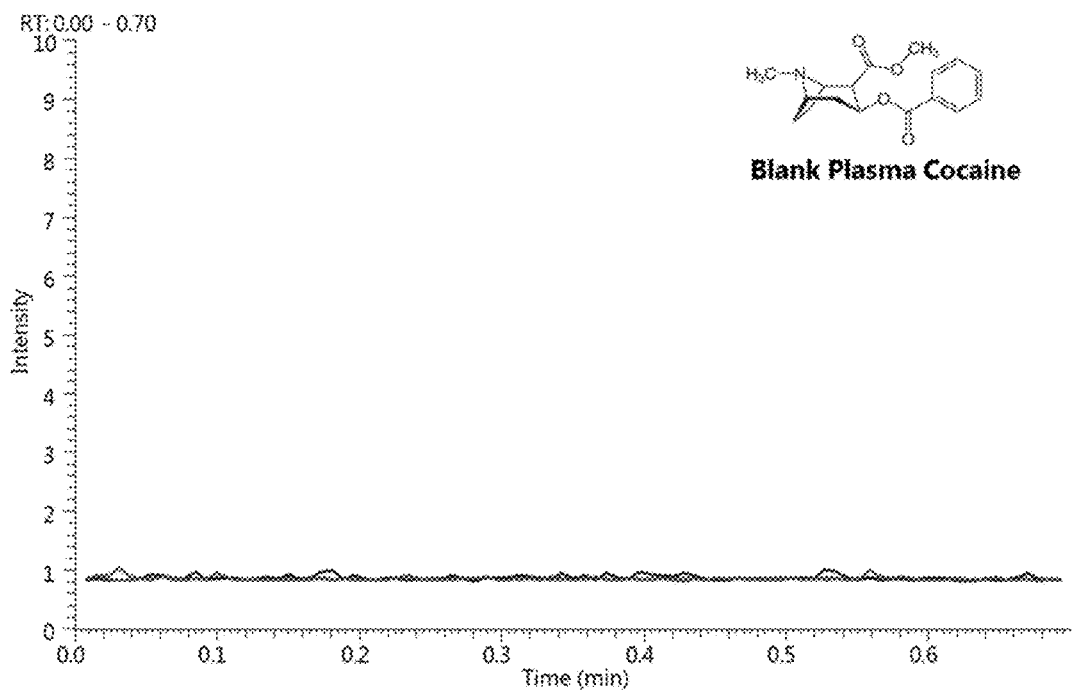
FIG. 8 shows blank chromatograms for three (3) independent blades. 1 min extraction from 1.5 mL of plasma. Analyses were performed using a Thermo TSQ on SRM mode. Monitoring for cocaine.
Figure 9:
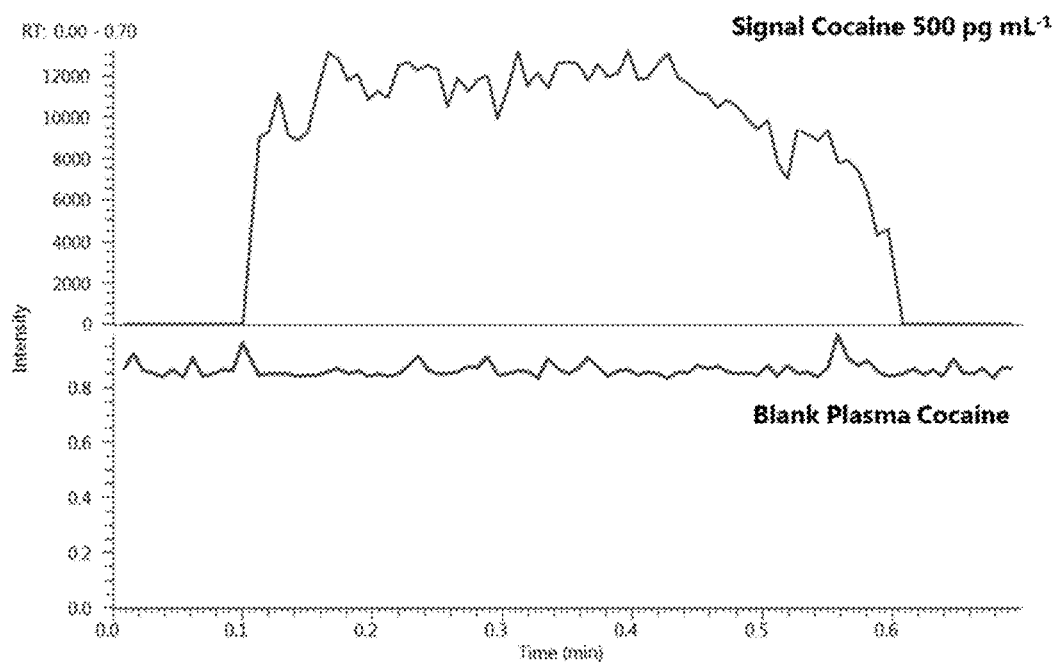
FIG. 9 shows chromatograms comparing the signal of blank versus extraction of 1 minute of plasma spiked 500 pg/mL of cocaine. Analyses were performed using a Thermo TSQ on SRM mode.
Figure 10A:
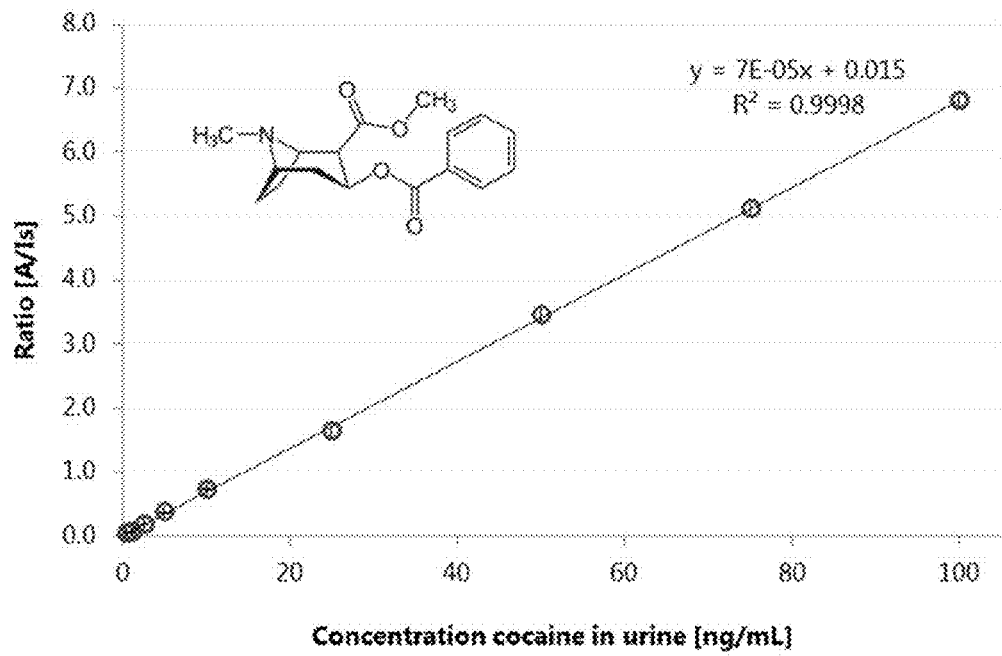
Figure 10B:
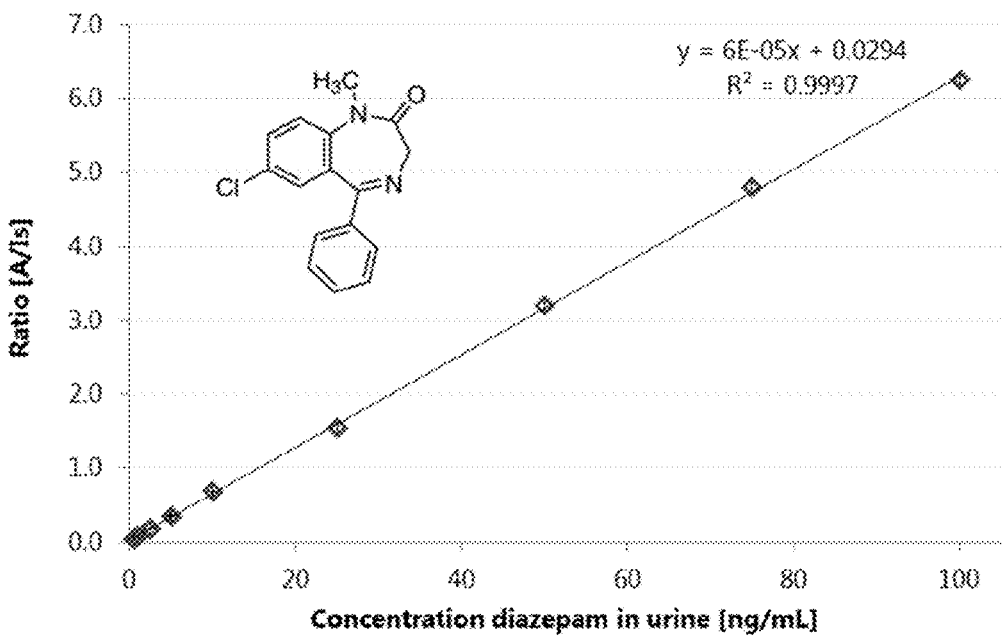
FIG. 10B is a graph illustrating quantitative analysis of urine spiked with diazepam (500 pg mL$^{-1}$ to 100 ng mL$^{-1}$) and its isotopologue [D5] diazepam (16 ng mL$^{-1}$). SD, standard deviation. RSD, relative standard deviation

Substrates, devices and methods disclosed herein may be used for the screening of pharmaceutical drugs or illicit compounds in biological samples. The coated solid substrates were used for the quantification of cocaine and diazepam in urine and plasma. Extractions were performed using coated solid substrates coated with C-18/PAN from a vial containing 1.5 mL of plasma spiked with the aforementioned analytes. The extraction time was 1 minute at an agitation speed of 3200 rpm (vortex agitation). The desorption of the analytes was performed using 17.5 µL of acidic methanol (0.1% formic acid). The wetting time was 34 seconds and subsequently a potential of 4 kV was applied to the solid substrate for ionization. FIGS. 8 and 9 illustrate the signals of blank plasma cocaine and signal cocaine (at 500 pg/mL).

Figure 11A:
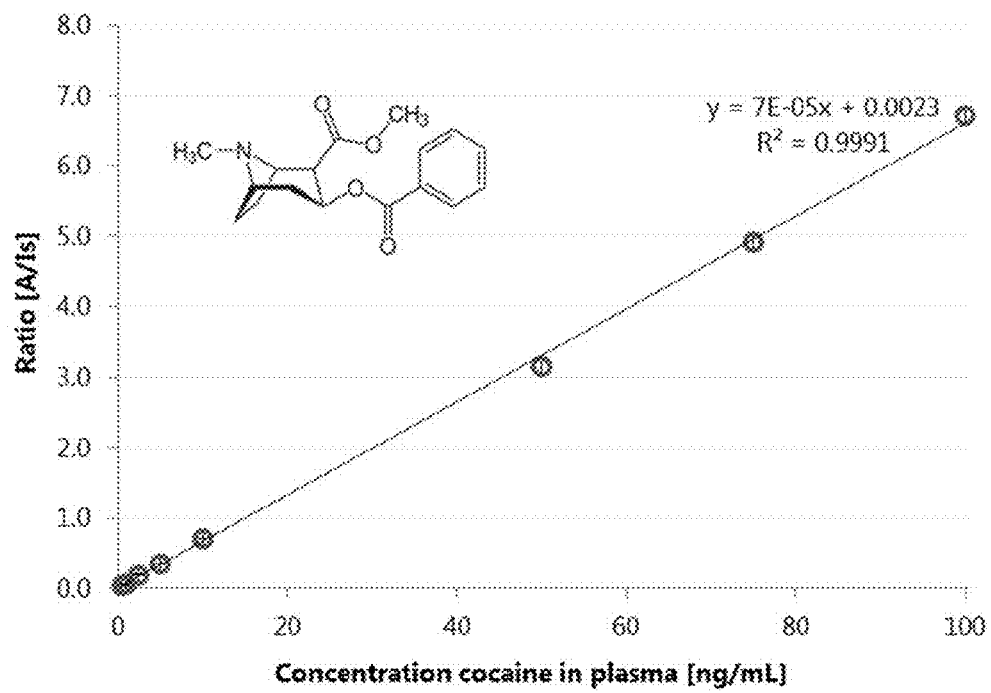
Figure 11B:
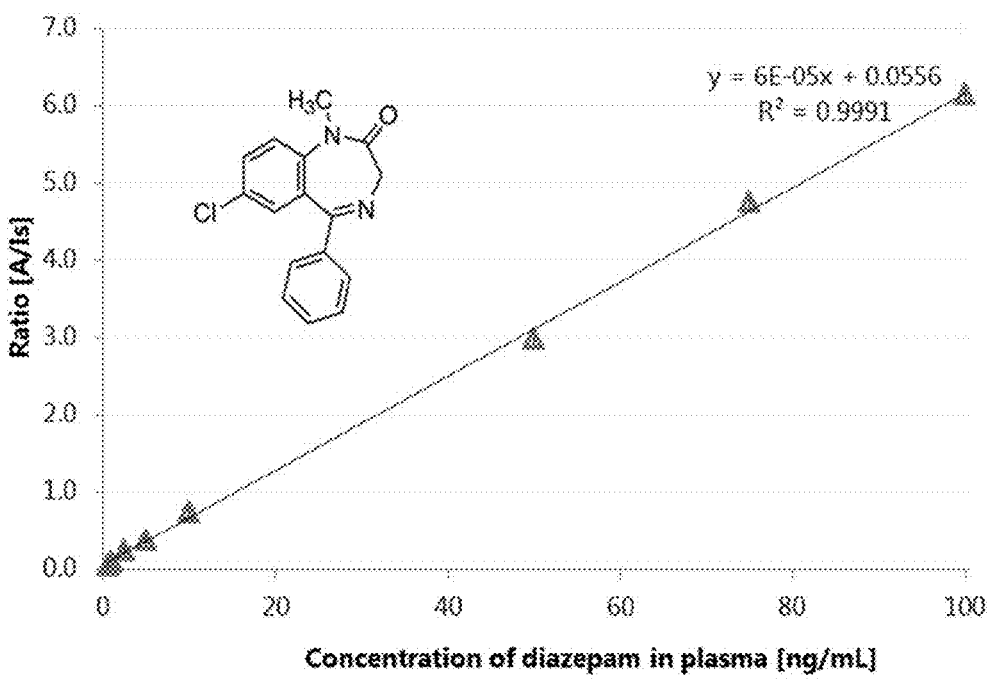
FIG. 11B is a graph illustrating quantitative analysis of plasma spiked with diazepam (500 pg mL$^{-1}$ to 100 ng mL$^{-1}$) and its isotopologue [D5] diazepam (16 ng mL$^{-1}$).
Figure 12:
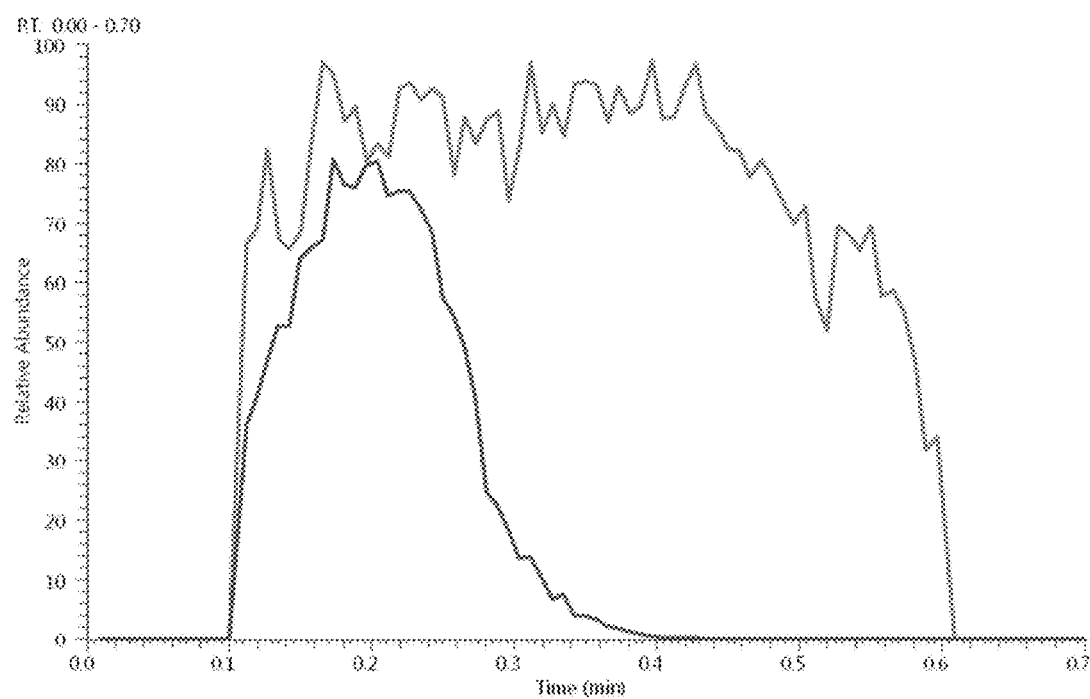
FIG. 12 shows ion chronograms of a blade sprayed after 10 seconds rinsing step in water (green) versus blade sprayed without rinsing (blue). 1 min extraction from 1.5 mL of PBS spiked with 500 pg mL$^{-1}$ of cocaine using a single blade. Analyses were performed using a Thermo TSQ on MRM mode.

As can be seen in FIGS. 10A, 10B, 11A and 11B, exceptional linearity was achieved for both cocaine (FIGS. 10A and 11A) and diazepam (FIGS. 10B and 11B) in both urine (FIGS. 10A and 10B) and plasma (FIGS. 11A and 11B). Similar to the results obtained in PBS, LOQs of 0.5 and 2 pg/mL were determined for cocaine in plasma and urine, respectively. In a comparison made with nano-pure water spiked with target analytes (FIG. 12), it was found that the rinsing step could be used to diminish ionization suppression from salts (e.g. salts from urine/PBS) or biomolecules attached to the coating surface (e.g. biomolecules from plasma).

In summary, by using a coated solid substrate according to the present disclosure to extract or transfer the analytes from the sample to the MS system, matrix effects for analytes with low binding are reduced and detection limits are similar independently of the matrix (e.g. cocaine, 5% protein binding). Sample clean-up provided by the described methods is convenient not only for quantitation purposes, but also to extend the operative time of the mass spectrometer, for example by minimizing instrument maintenance, and providing steady instrumental sensitivity. Unlike cocaine, LOD/LOQ for DZP in plasma were 15 and 50 ppt, respectively. Although the quantification limit is higher in comparison to urine and PBS (LOQ 5 ppt), it is worth emphasizing that DZP is 98% bound to plasma proteins and, as an SPME device, the described method extracts via free concentration of analyte in the sample. Last but not least important, the total analysis time (extraction from a sample without pre-treatment, rinsing, desorption/ionization, peak integration, and quantitation of total concentration) was less than 3 minutes per sample when performing manual operation of the blades.

Experiment 6

Figure 13A:
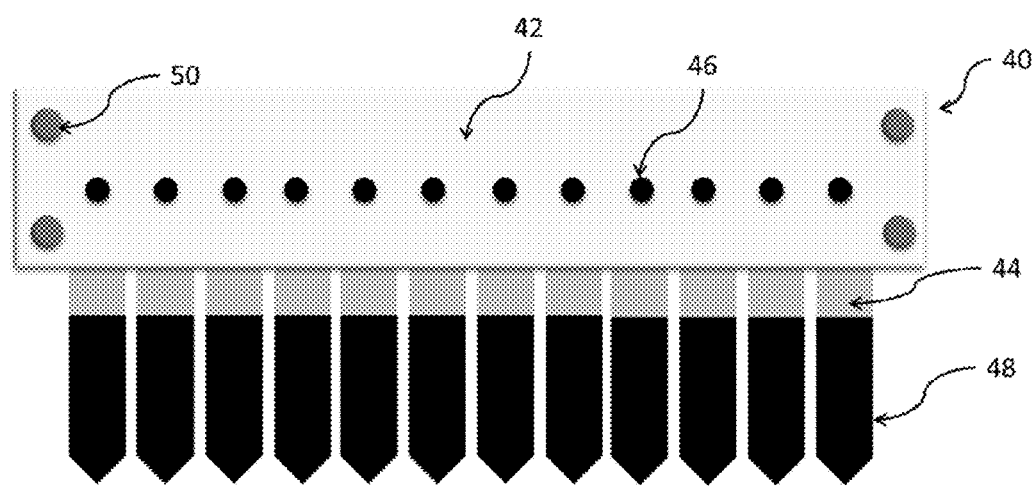
FIGS. 13A and 13B illustrates 12-blade spray configuration for high-throughput analysis using a 96-well autosampler from the top view (FIG. 13A) and side view (FIG. 13B).
Figure 13B:
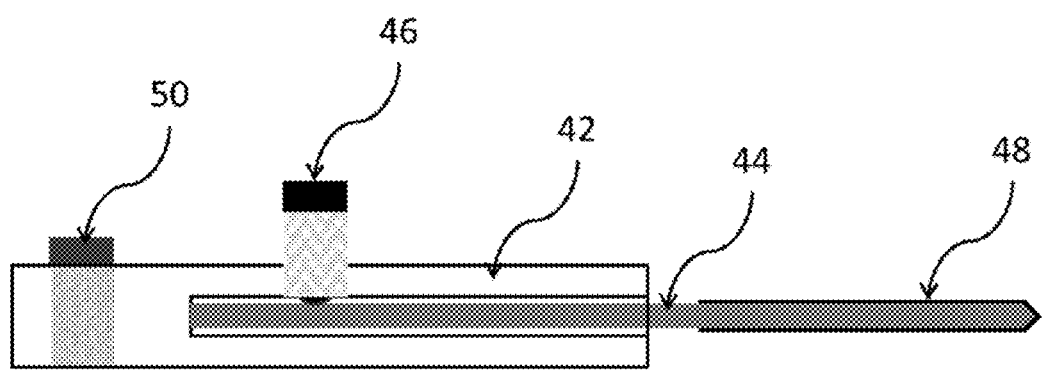

In order to meet the demands of high-throughput analysis, a fully automated desorption or ionization unit may be used. An exemplary holder for such a desorption or ionization unit is illustrated in FIGS. 13A (top view) and 13B (lateral view). The exemplary holder (40) includes a non-conductive portion (42) and holds 12 coated solid substrates (44) using ball end clamping screws (46). The coated solid substrates are 2 mm wide and the coated portion (48) is 15 mm long. The holder (40) holds the coated solid substrates (44) in a configuration that allows them to be inserted into one row of a 96-well plate. The holders (40) include magnets (50) that are positioned to attach one holder to an adjacent holder. The holder (40) is sized and shaped so that 8 holders attached together allow the coated solid substrates to be inserted into the 8 rows of a 96-well plate. The 8 attached holders, each holding 12 coated solid substrates, allow each of the 96 coated solid substrates to be inserted into each of the 96 wells.

One of the attached holders holding the coated solid substrate may be separated from the other holders by, for example, an autosampler. Each coated solid substrate may be positioned in front of the desorption and ionization unit to produce ionized droplets for mass spectrometry analysis.

By automating the extraction and/or rinsing step with a 96-well autosampler, and the mass spectrometry introduction step with the aforementioned LC/MS apparatus, total analysis time of 45 seconds or less can be attained per sample. Hence, the analysis of more than thousand samples per day is predicted using such a system. The coupling of blade spray to mass spectrometry using automated systems may offer one or more benefits, such as: analysis times similar to conventional "non-sample preparation" ambient mass spectrometry methods (e.g. paper spray), or lower detection limits with negligible matrix interferences.

Experiment 7

Figure 14A:
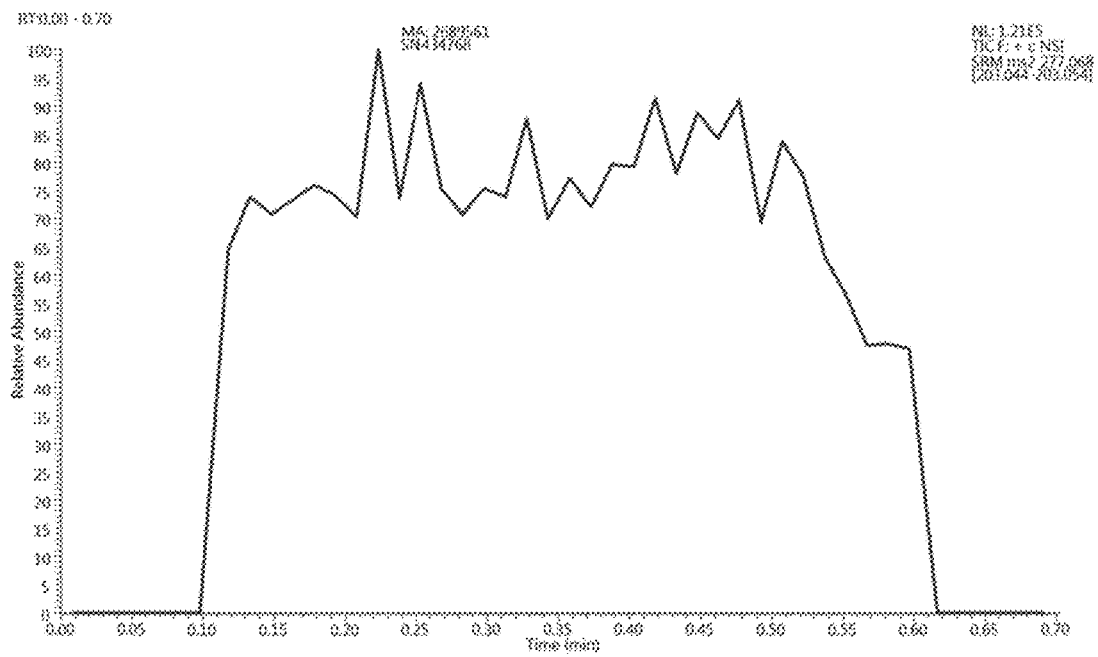
FIGS. 14A, 14B and 14C show ion chronograms of three controlled substances: clenbuterol (FIG. 14A), 6-acetylcodeine (FIG. 14B), and toremifene (FIG. 14C). 1 min extractions were performed using vortex agitator set-up at maximum speed (3200 rpm). Simultaneous extraction from 1.5 mL of PBS spiked with 20 ng mL$^{-1}$ of 21 substances described on Table 2. Analyses were performed using Thermo TSQ on MRM mode.
Figure 14B:
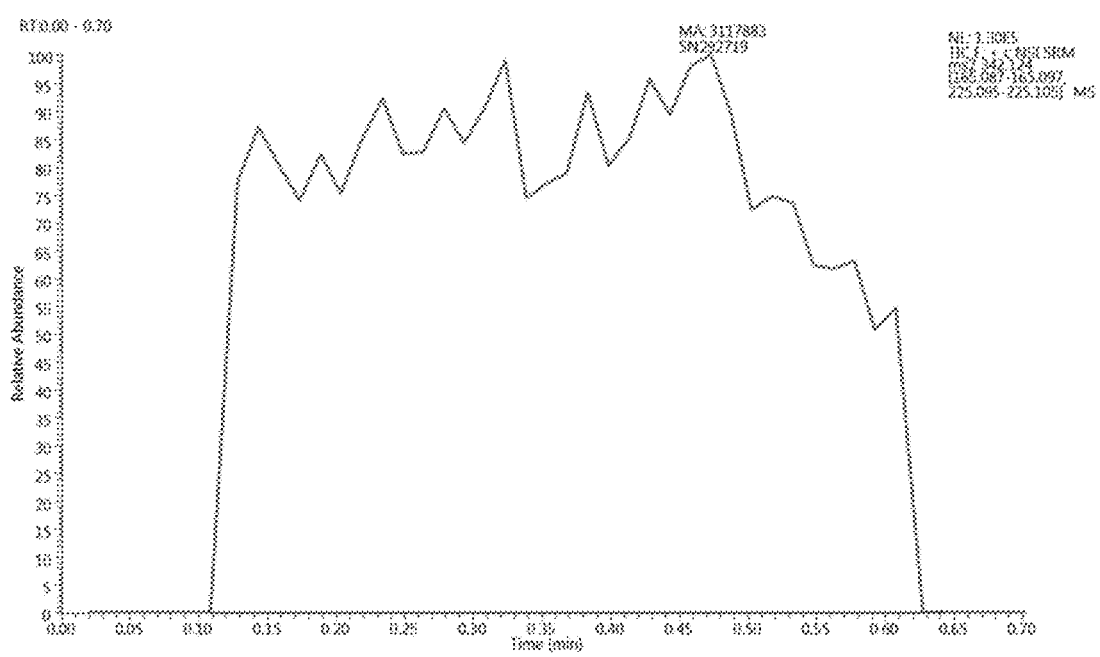
Figure 14C:
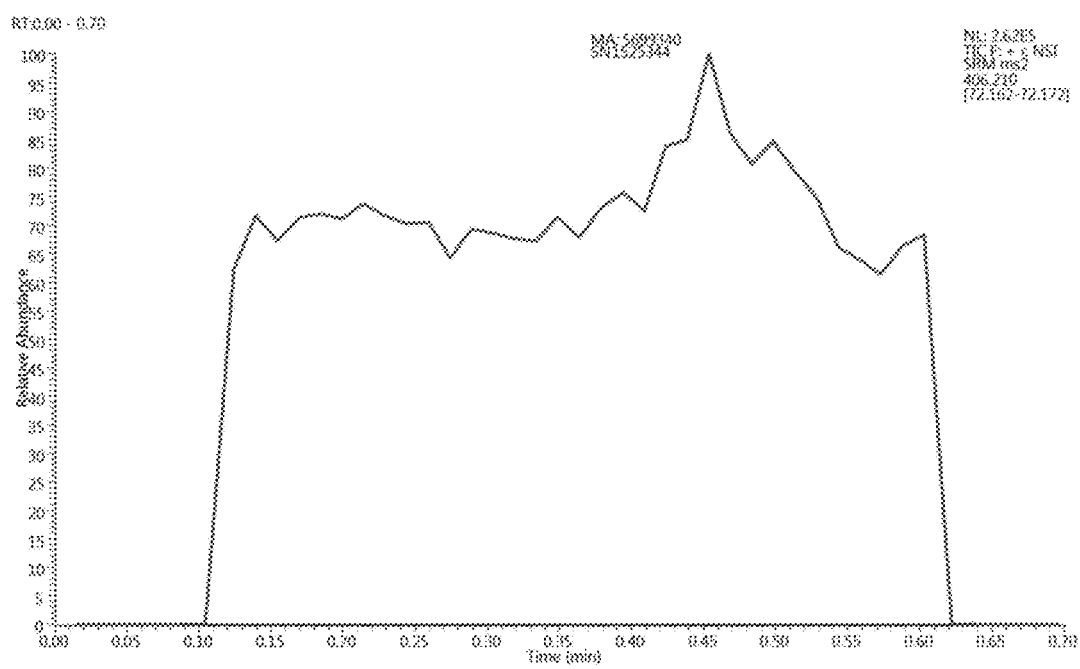

Exemplary coated solid substrates were used to screen 21 compounds controlled by the World Anti-Doping Agency (WADA) and the United Nations Office of Drugs and Crime (UNODC). Extractions were performed using coated solid substrates coated with C-18/PAN from a vial containing 1.5 mL of plasma spiked at 20 ppb with the analytes mentioned in Table 2. The extraction time was 1 minute at an agitation speed of 3200 rpm (vortex agitation). The desorption of the analytes was performed using 17.5 µL of acidic methanol (0.1% formic acid). The wetting time was 34 seconds and subsequently a potential of 4 kV was applied to the solid substrate for ionization. Selected reaction monitoring (SRM) was used to uniquely identify each substance. SRM is a method used in tandem mass spectrometry in which an ion of a particular mass is selected in the first stage of a tandem mass spectrometer and an ion product of a fragmentation reaction of the precursor ion is selected in the second mass spectrometer stage for detection. Based on the results obtained for cocaine PBS (FIG. 5), LOQ were tentatively estimated for all compounds (Table 2). Although desorption or ionization conditions were not optimized for each analyte, all substances were detected at 20 ppb and 14 compounds provided hypothetical LOD lower than 5 ppt (e.g. clenbuterol, 6-acetylcodeine, and toremifene, FIGS. 14A-C, respectively). The capability of the disclosed method to simultaneously screen multiple substances of interest in a single analysis, without sacrificing sensitivity or increasing the analysis time, is an outstanding example of methods disclosed herein.

TABLE 2

MS/MS parameters used for the analysis of 21 WADA controlled substances in positive mode (polarity+), as well as instrumental response of $C_{18}$-PAN CBS in plasma tandem mass spectrometry analysis.

| Compound name | Log P | Parent ion (m/z) | Product ion (m/z) | S-lenses | Collision energy | LOD * |
|---|---|---|---|---|---|---|
| Amphetamine | 1.76 | 136.099 | 91.114 | 17 | 36 | 212 |
| Methamphetamine | 2.07 | 150.112 | 91.120 | 19 | 45 | 2 |
| Salbutamol | 0.64 | 240.143 | 148.103 | 18 | 59 | 3 |
| Propranolol | 3.48 | 260.123 | 116.138 | 17 | 89 | 8 |
| Metoprolol | 1.60 | 268.140 | 116.146 | 18 | 94 | 66 |
| Trenbolone | 2.27 | 271.133 | 165.106 | 56 | 97 | 30 |
| Clenbuterol | 2.61 | 277.068 | 203.049 | 15 | 70 | 0.4 |
| Morphine | 0.89 | 286.119 | 152.092 | 61 | 110 | 711 |
| Testosterone | 3.32 | 289.157 | 97.123 | 21 | 91 | 15 |
| Exemestane | 3.70 | 297.173 | 121.118 | 19 | 72 | 33 |
| Codeine | 1.20 | 300.105 | 152.092 | 64 | 104 | 2 |
| Cocaine | 2.30 | 304.142 | 182.173 | 18 | 87 | 0.1 |
| Bisoprolol | 2.14 | 326.160 | 116.135 | 17 | 102 | 0.5 |
| 6-acetylmorphine | 0.42 | 328.126 | 165.092 | 37 | 122 | 1 |
| Stanozolol | 5.53 | 329.229 | 81.108 | 44 | 130 | 1 |
| Strychnine | 1.93 | 335.155 | 184.129 | 36 | 136 | 1 |
| 6-acetylcodeine | 2.08 | 342.124 | 165.092 | 45 | 165 | 0.3 |
| Formoterol | 2.20 | 345.133 | 121.090 | 32 | 85 | 0.1 |
| Heroin | 1.52 | 370.133 | 165.097 | 48 | 119 | 1 |
| Toremifene | 6.80 | 406.210 | 72.167 | 24 | 108 | 0.2 |
| GW501516 | 6.29 | 454.091 | 257.068 | 29 | 108 | 3 |

LOD *, limit of detection estimated (pg/mL).

In the preceding description, for purposes of explanation, numerous details are set forth in order to provide a thorough understanding of the embodiments. However, it will be apparent to one skilled in the art that these specific details are not required. Accordingly, what has been described is merely illustrative of the application of the described embodiments and numerous modifications and variations are possible in light of the above teachings.

Since the above description provides example embodiments, it will be appreciated that modifications and variations can be effected to the particular embodiments by those

What we claimed is:

1. A device for generating ionized molecules for analysis in a mass spectrometer, the device comprising:
a solid substrate having one or more edges and a coated area that is coated with an extraction phase comprising an extraction polymer, the extraction phase coating the solid substrate over an area from about 0.1 mm$^2$ to about 100 mm$^2$.

2. The device according to claim 1, wherein the extraction polymer is a biocompatible polymer.

3. The device according to claim 1, wherein the solid substrate has at least two edges that meet at an angle from about 8° to about 90°.

4. The device according to claim 1, wherein the solid substrate has a plurality of edges that meet to form a plurality of points.

5. The device according to claim 1, wherein the solid substrate has a homogeneous thickness from about 0.01 mm to about 2 mm.

6. The device according to claim 1, wherein the solid substrate has:
a. a length from about 1 to about 10 cm;
b. a width from about 0.1 to about 5 mm; and
c. a thickness from about 0.1 mm to about 2 mm.

7. The device according to claim 1, wherein the solid substrate comprises a metal, a metal alloy, or a polymer.

8. The device according to claim 1, wherein the extraction phase coating the solid substrate comprises solid phase micro-extraction (SPME) porous particles having a surface able to absorb a molecule from a sample.

9. The device according to claim 1 wherein the extraction phase is homogeneous in thickness and composition over the coated area.

10. The device according to claim 1 wherein the extraction phase is inhomogeneous along the length of the mass spectrometry probe.

11. The device according to claim 10, wherein the extraction phase is inhomogeneous along the length of the solid substrate due to variations in the composition of the extraction phase along the length of the solid substrate, or due to variations in the thickness of the extraction phase along the length of the solid substrate.

12. The device according to claim 1, wherein the extraction phase has a thickness from about 0.2 µm to about 100 µm.

13. The device according to claim 8, wherein the extraction phase has a thickness sufficient to include one or two layers of particles.

14. The device according to claim 1, wherein the coated solid substrate has a first side coated with a first extraction phase, and a second side coated with a second extraction phase that is different from the first extraction phase.

15. The device according to claim 14, wherein the first extraction phase comprises extractive particles that provide hydrophobic interactions, and the second extraction phase comprises extractive particles that provide hydrophilic interactions.

16. The device according to claim 1, wherein the extraction phase is loaded with an internal standard.

17. The device according to claim 1, wherein the solid substrate is square or rectangular in cross-section.

18. A mass spectrometry system comprising:
a device according to claim 1;
a desorption solvent covering at least a portion of the extraction phase;
a high voltage source; and
a mass analyzer;
wherein the device is connected to the high voltage source, and no solvent is applied to the device during ionization.

19. A method for analyzing a molecule previously extracted from a sample onto the extraction phase of a device according to claim 1, the method comprising:
applying a voltage to the device that is sufficiently high to desorb and expel ions of molecules from the extraction phase, while keeping the coated solid substrate separate from a flow of solvent; and
analyzing the expelled ions by mass spectrometry.

* * * * *

UNITED STATES PATENT AND TRADEMARK OFFICE
CERTIFICATE OF CORRECTION

PATENT NO. : 9,733,234 B2
APPLICATION NO. : 14/738688
DATED : August 15, 2017
INVENTOR(S) : Janusz B. Pawliszyn and German Augusto Gomez Rios It is certified that error appears in the above-identified patent and that said Letters Patent is hereby corrected as shown below:

On the Title Page

Page 2, First Column, First Line, Item (60) Continued:
"application No. 13/478,295, filed on May 23, 2013," should read --application No. 13/478,295, filed on May 23, 2012,--

Signed and Sealed this
Twenty-seventh Day of March, 2018

Andrei Iancu
*Director of the United States Patent and Trademark Office*